US012599141B2

(12) United States Patent　(10) Patent No.: US 12,599,141 B2
Steinmetz et al.　(45) Date of Patent: Apr. 14, 2026

(54) ROD-SHAPED PLANT VIRAL NANOPARTICLES OR VIRUS-LIKE PARTICLES FOR AGRICULTURAL APPLICATIONS

(71) Applicant: CASE WESTERN RESERVE UNIVERSITY, Cleveland, OH (US)

(72) Inventors: Nicole F. Steinmetz, San Diego, CA (US); Paul L. Chariou, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 500 days.

(21) Appl. No.: 16/306,855

(22) PCT Filed: Jun. 5, 2017

(86) PCT No.: PCT/US2017/035957
§ 371 (c)(1),
(2) Date: Dec. 3, 2018

(87) PCT Pub. No.: WO2017/210682

PCT Pub. Date: Dec. 7, 2017

(65) Prior Publication Data

US 2019/0141992 A1　May 16, 2019

Related U.S. Application Data

(60) Provisional application No. 62/345,212, filed on Jun. 3, 2016.

(51) Int. Cl.
| | |
|---|---|
| *A01N 63/40* | (2020.01) |
| *A01N 25/10* | (2006.01) |
| *A01N 25/24* | (2006.01) |
| *A01N 25/28* | (2006.01) |
| *A01N 25/32* | (2006.01) |
| *A01N 25/34* | (2006.01) |
| *A01N 43/90* | (2006.01) |
| *A61K 47/30* | (2006.01) |
| *A61K 9/51* | (2006.01) |

(52) U.S. Cl.
CPC ............. *A01N 63/40* (2020.01); *A01N 25/10* (2013.01); *A01N 25/24* (2013.01); *A01N 25/28* (2013.01); *A01N 25/32* (2013.01); *A01N 25/34* (2013.01); *A01N 43/90* (2013.01); *A61K 47/30* (2013.01); *A01N 2300/00* (2013.01); *A61K 9/5184* (2013.01)

(58) Field of Classification Search
CPC ........ A01N 25/28; A01N 25/34; A01N 43/90; A01N 63/40; A01N 2300/00; A01N 25/10; A01N 25/24; A01N 25/32; A61K 9/5184; A61K 47/30
See application file for complete search history.

(56) References Cited

U.S. PATENT DOCUMENTS

| | | | |
|---|---|---|---|
| 5,004,606 A | 4/1991 | Frincke | |
| 5,723,750 A * | 3/1998 | Stubbs ................. | C07K 14/005 |
| | | | 435/320.1 |
| 9,925,281 B2 | 3/2018 | Steinmetz et al. | |
| 10,086,095 B2 | 10/2018 | Steinmetz et al. | |
| 10,207,014 B2 | 2/2019 | Steinmetz et al. | |
| 10,478,510 B2 | 11/2019 | Steinmetz | |
| 11,020,497 B2 | 6/2021 | Steinmetz et al. | |
| 11,167,047 B2 | 11/2021 | Steinmetz et al. | |
| 11,253,610 B2 | 2/2022 | Steinmetz | |
| 2003/0181355 A1* | 9/2003 | Glenn .................... | A61K 38/06 |
| | | | 514/3.7 |
| 2004/0162220 A1 | 8/2004 | Charudattan et al. | |
| 2005/0019270 A1 | 1/2005 | Finlay et al. | |
| 2007/0160628 A1* | 7/2007 | Birkett ..................... | C12N 7/00 |
| | | | 424/204.1 |
| 2007/0258889 A1 | 11/2007 | Douglas | |
| 2007/0284545 A1 | 12/2007 | Isacsson et al. | |
| 2010/0183504 A1 | 7/2010 | Chen | |
| 2015/0033418 A1* | 1/2015 | Lommel ................ | A01N 25/28 |
| | | | 800/312 |
| 2015/0265729 A1 | 9/2015 | Steinmetz et al. | |

(Continued)

FOREIGN PATENT DOCUMENTS

| | | |
|---|---|---|
| JP | 2009524699 A | 7/2009 |
| WO | 01/18199 A1 | 3/2001 |

(Continued)

OTHER PUBLICATIONS

Love et al. (The use of tobacco mosaic virus and cowpea mosaic virus for the production of novel metal nanomaterials, Virology 449 (2014), pp. 133-139) (Year: 2014).*

Miermont et al., "Cowpea Mosaic Virus Capsid: A promising Carrier for the Development of Carbohydrate Based Antitumor Vaccines", Chem. Eur. J., 2008, vol. 14, pp. 4939-4947.

Sheen et al., "Stimulating Antitumor Immunity with Nanoparticles", Wiley Interdiscip Rev Nanomed Nanobiotechnol, Oct. 2014, vol. 6, pp. 496-505.

Office action for Chinese Patent Application No. 201580063662.6, dated Mar. 4, 2020.

(Continued)

*Primary Examiner* — Bethany P Barham
*Assistant Examiner* — Danielle Johnson
(74) *Attorney, Agent, or Firm* — Tarolli, Sundheim, Covell & Tummino LLP

(57) ABSTRACT

An agricultural composition includes a plurality of rod-shaped plant viral nanoparticles (VNPs) and/or virus-like particles (VLPs), each VNP and/or VLP having an exterior surface and an interior surface that extend from a first end to a second of the rod-shaped VNP and/or VLP, the interior surface defining a channel that extends through rod-shaped VNP from the first end to the second end; and at least one agrochemical agent attached or conjugated to the interior and/or exterior surface of the rod-shaped plant VNPs and/or VLPs.

9 Claims, 7 Drawing Sheets

(56) References Cited

U.S. PATENT DOCUMENTS

| | | | |
|---|---|---|---|
| 2020/0179468 A1 | 6/2020 | Steinmetz |
| 2022/0211881 A1 | 7/2022 | Steinmetz |

FOREIGN PATENT DOCUMENTS

| | | | | |
|---|---|---|---|---|
| WO | 200118199 A1 | 3/2001 | | |
| WO | 2001/0026682 A2 | 4/2001 | | |
| WO | 2003092623 A2 | 11/2003 | | |
| WO | 2012078069 A1 | 6/2012 | | |
| WO | WO-2013158620 A1 * | 10/2013 | ............ | A01N 25/26 |
| WO | 2013181557 A1 | 12/2013 | | |
| WO | 2015/0039255 A1 | 3/2015 | | |
| WO | 2016/073972 A1 | 5/2016 | | |

OTHER PUBLICATIONS

Office action for European Patent Application No. 15 857 504.3-1111, dated Mar. 18, 2020.

Yildiz et al., "Applications of viral nanoparticles in medicine", Current Opinion in Biotechnology, vol. 22, Issue 6, pp. 901-908.

Aljabali, et al., "CPMV-DOX Delivers", Molecular Pharmaceutics, 2013, 10, pp. 3-10.

Wen, et al., "Interior Engineering of a Viral Nanoparticle and its Tumor Homing Properties" Macromolecules, vol. 13, No. 12, Dec. 2012.

Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.

Brennan, et al., "Cowpea Mosaic Virus as a Vaccine Carrier of Heterologous Antigens", Molecular Biotechnology, vol. 17, No. 1, Jan. 2001.

Gonzalez, et al., "Interaction of Cowpea Mosaic Virus (CPMV) Nanoparticles with Antigen Presenting Cells in Vitro and In Vivo", Plos One, vol. 4, No. 11, Nov. 2009.

Izotte, et al., "Plant-derived viral-like nanoparticle immunotherapy suppress development of metastatic lung cancer", Journal of Immunology, vol. 194, Issue 1 Supplement, May 2015.

Patrick H. Lizotte, "Novel approaches to targeting innate immunity for cancer immunotherapy", Proquest Dissertations Publishing, May 2015.

Supplementary European Search Report for Patent Application No. 15857504.3-1111/3215520, dated May 28, 2018.

International Search Report for Application No. PCT/US15/59675.

Smyth et al. Treatment of rapidly growing K-BALB and CT26 mouse tumours using Semliki Forest virus and its derived vector. Gene Therapy (2005) 12, 147-159.

Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.

Applicant: Case Western Reserve University; "Cancer Immunotherapy Using Virus Particles"; Office Action, dated Aug. 4, 2020; 3 pgs.

Applicant: Case Western Reserve University; "Plant Virus Particles for Delivery of Antimitotic Agents"; Extended European Search Report; dated Aug. 17, 2020; 11 pgs.

Canan Uluog, et al.: "Intermediate dose of methotrexate toxicity in non-Hodgkin lymphoma", General Pharmacology, vol. 32, 1999, pp. 215-218, XP55711259.

Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.

Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.

Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].

Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.

Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.

Francisco, Joseph A., et al.; "cAC10-vcMMAE, an anti-CD30-monomethyl auristatin E conjugate with potent and selective anti-tumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.

Shivprasad et al., "Hererologous Sequences Greatly Affect Foreign Gene Expression in Tobacco Mosaic Virus-Based Vectors," Virology, Mar. 15, 1999 (Mar. 15, 1999). vol. 255, pp. 312-323.

Chariou, et al., "Delivery of Pesticides to Plant Parasitic Nematodes Using Tobacco Mild Green Mosaic Virus as a Nanocarrier," ACS Nano, May 23, 2017 (May 23, 2017), vol. 11, No. 5 pp. 4719-4730.

Czapar, et al., "Tobacco Mosaic Virus Delivery of Phenanthriplatin for Cancer Therapy," ACS Nano, Mar. 28, 2016 (Mar. 28, 2016), vol. 10, No. 4, pp. 4119-4126.

Lee, et al., "Genetic Engineering and Chemical Conjugation of Potato Virus X," Methods in Molecular Biology, Chapter: Virus Hybrids as Nanomaterials, Oct. 30, 2013 (Oct. 30, 2013), vol. 1108, pp. 3-21.

Applicant: Case Western Reserve University; "Cancer Immunotherapy Using Virus Particles"; European Patent Application No. 18764856.3 for Supplementary European Search Report dated Dec. 22, 2020; 8 pgs.

Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.

Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.

Nicole F.Steinmetz; "Viral Nanoparticle Multimers"; U.S. Appl. No. 14/761,444, filed Jul. 16, 2015; Final Office Action dated Mar. 11, 2021; 11 pgs.

Czapar, Anna et al. Tobacco Mosaic Virus Delivery of Phenanthriplatin for Cancer therapy. American Chemical Society. Nano 2016 (10) pp. 4119 4126 (Year: 2016).

Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).

Le, Duc et al. Chemical addressability of potoato virus X for its applications in bio/nanotechnology. El Sevier. Journal of Structural Biology 200 (2017). pp. 360-368. (Year: 2017).

Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).

Nicole F. Steinmetz, U.S. Appl. No. 16/998,210, filed Aug. 7, 2020; Non-Final OA dated Dec. 7, 2022.

Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).

Bruckman et al. (Nano Letters. Mar. 2014; 14: 1551-1558).

Mamura et al. ("FOXA 1 promotes tumor progression in prostate cancer via the insulin-like growth factor binding protein 3 pathway." (2012).

Lam, et al. (WIREs Nanomed Nanobiotechnol Jan./Feb. 2018 vol. 10: 1-18).

Mitoxantrone. Drug Bank Online. Website. https://go.drugbank.com/drugs/DB01204. (Accessed Dec. 15, 2022) (Year: 2022).

Mosquera et al. (Acc. Chem. Res. 2018, 51, 9, 2305-2313 Publication Date: Aug. 29, 2018.

Nicole F.Steinmetz; U.S. Appl. No. 16/597,509, filed Oct. 9, 2019; Non-Final Office Action, dated Dec. 27, 2022; 12 pgs.

Nicole F.Steinmetz; U.S. Appl. No. 16/759,652, filed Apr. 27, 2020; Final Office Action, dated Dec. 12, 2022; 15 pgs.

(56)                    References Cited

OTHER PUBLICATIONS

Nicole F.Steinmetz; U.S. Appl. No. 17/129,463, filed Dec. 21, 2020; Non-Final Office Action, dated Dec. 8, 2022; 32 pgs.

Nicole F.Steinmetz;U.S. Appl. No. 17/522,182, filed Nov. 9, 2021; Non-Final Office Action, dated Jan. 5, 2023; 27 pgs.

Nicole F.Steinmetz; U.S. Appl. No. 17/677,147, filed Feb. 22, 2022; Non-Final Office Action, dated Jan. 13, 2023; 22 pgs.

Pellico et al. (Contrast Media and Molecular Imaging. 2019; Article ID 1845637: 1-13).

Pretto et al. ("Versatile reversible cross-linking strategy to stabilize CCMV virus like particles for efficient siRNA delivery." Bioconjugate chemistry 30.12 (2019): 3069-3077).

Royston et al. (Journal of Colloidal and Interface Science. 2009; 332: 402-407).

Tamoxifen. Drug Bank Online. Website. https://go.drugbank.com/drugs/DB00675. (Accessed: Dec. 15, 2022) (Year: 2022).

Temming et al. (bioconjugate Chemistry. 2006; 17: 1385-1394).

Kiao et al. (International Journal of Molecular Medicine. 2016; 38: 1319-326).

Zhang et al. (Theranostics. 2018; 8 (9): 2521-2548).

Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.

Applicant: Case Western Reserve University; "Cancer Immunotherapy Using Virus Particles"; European Patent Application No. 21201960.8; Extended European Search Report dated Jan. 19, 2022; 11 pgs.

Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.

Gonzalez Maria Jet Al: "Interaction of Cowpea Mosaic Virus (CPMV) Nanoparticles with Antigen Presenting Cells In Vitro and In Vivo", Plos One, vol. 4, No. 11, Nov. 2009 (Nov. 2009), KP002780311, ISSN: 1932-6203.

Patrick h. Iizotte: "Novel approaches to targeting innate immunity for cancer Immunotherapy", Proquest Dissertations Publishing, May 2015 (May 2015), XP002780316, Retrieved from the Internet: URL:https://search.proquest.com/docview/16 95832154?pq-origsite=gscholar [retrieved on Apr. 19, 2018].

Saunders Ket Al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].

\* cited by examiner

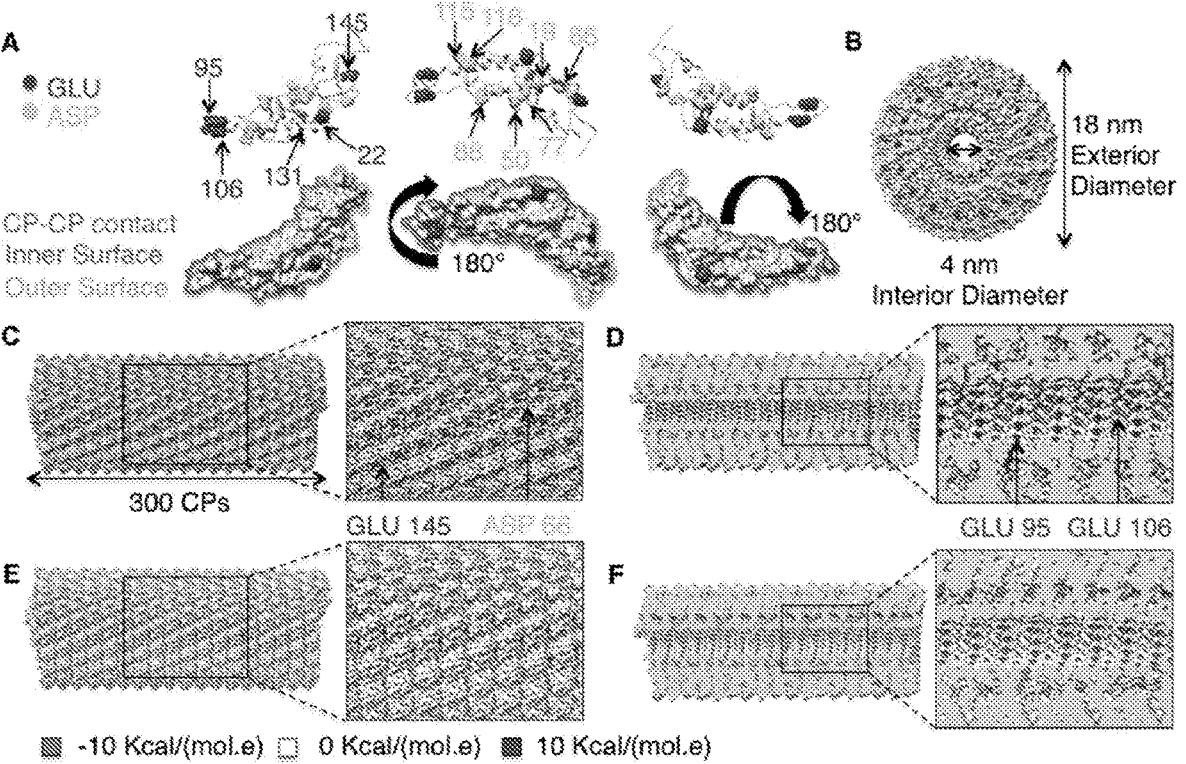
Fig. 1A-F

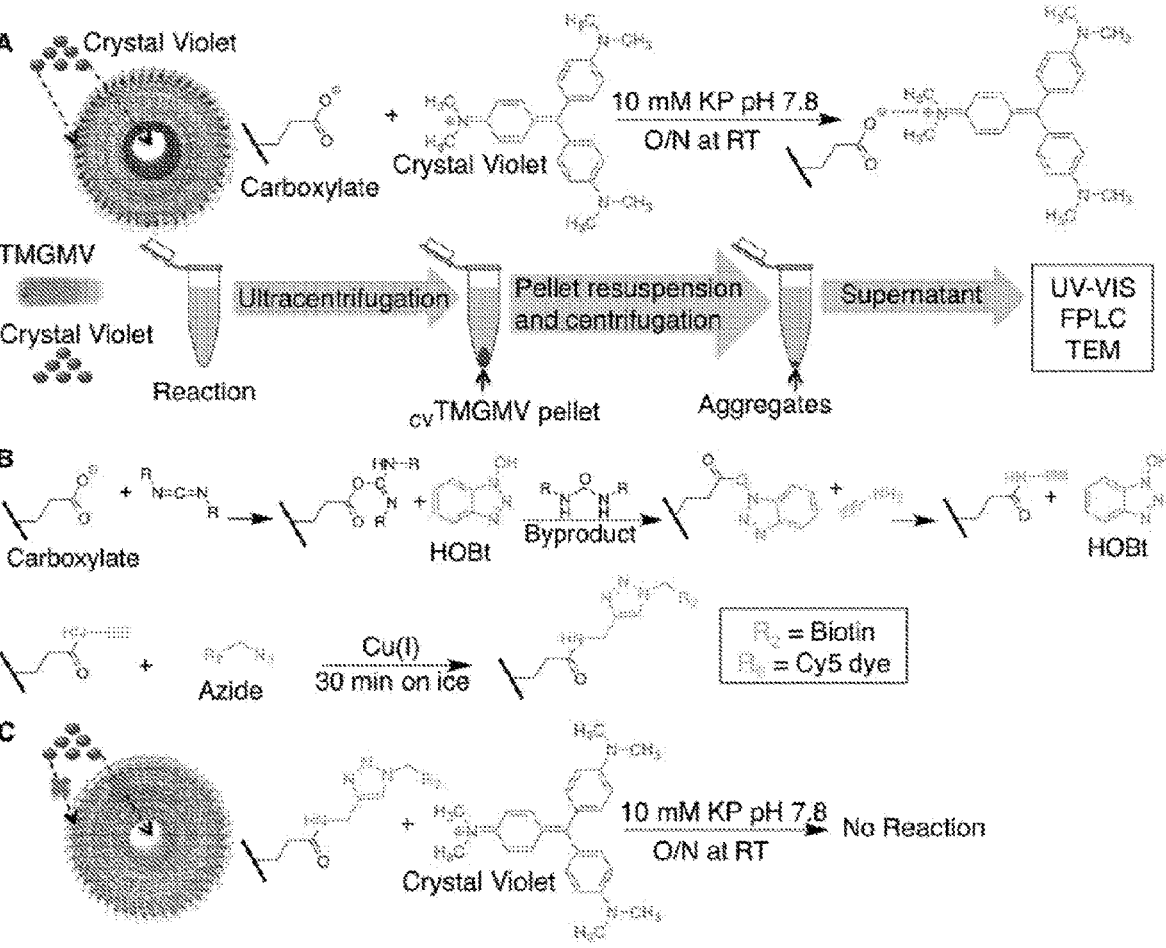
Figs. 2A-C

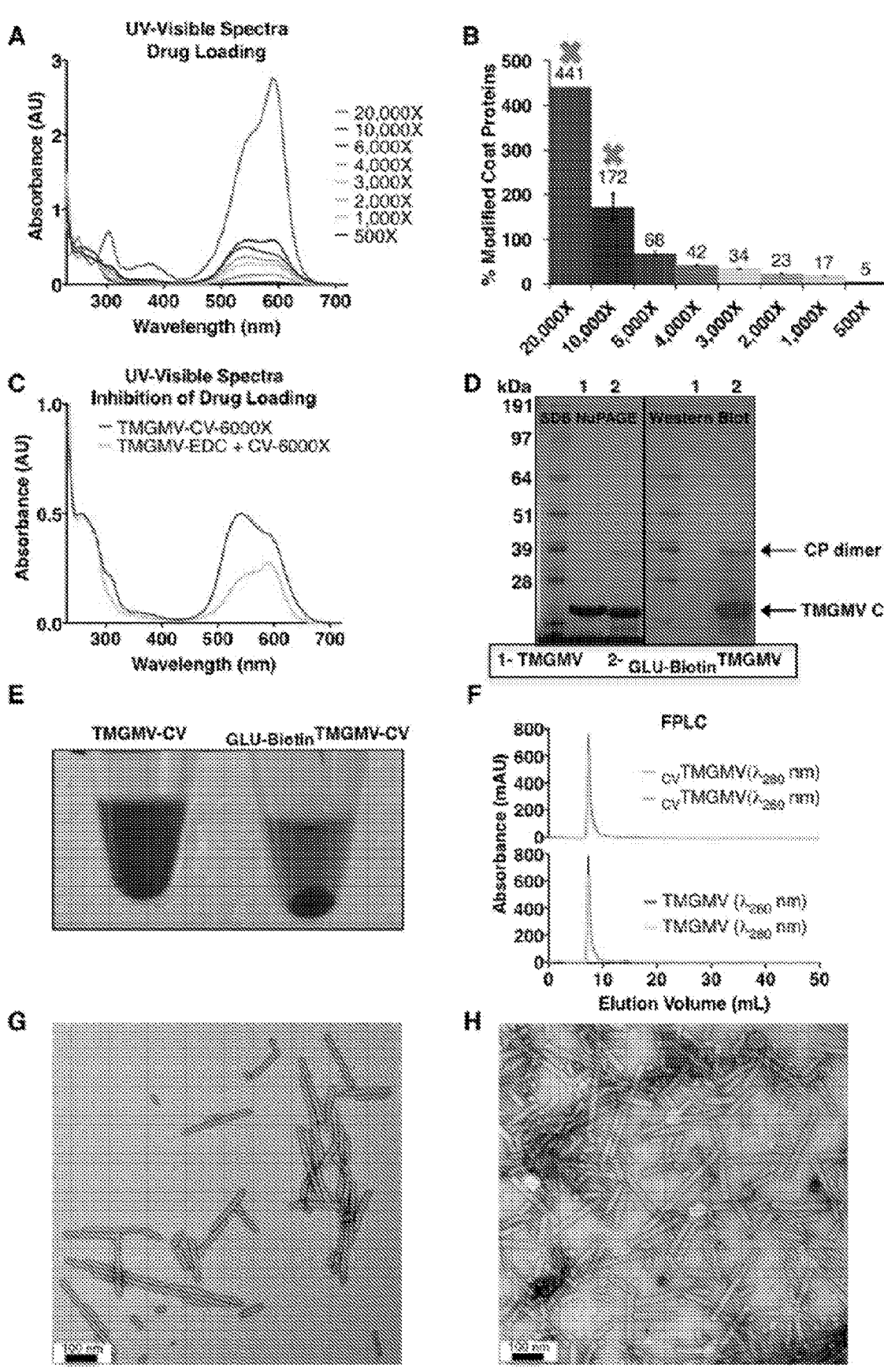
Figs. 3A-H

A
Cumulative % Drug Release
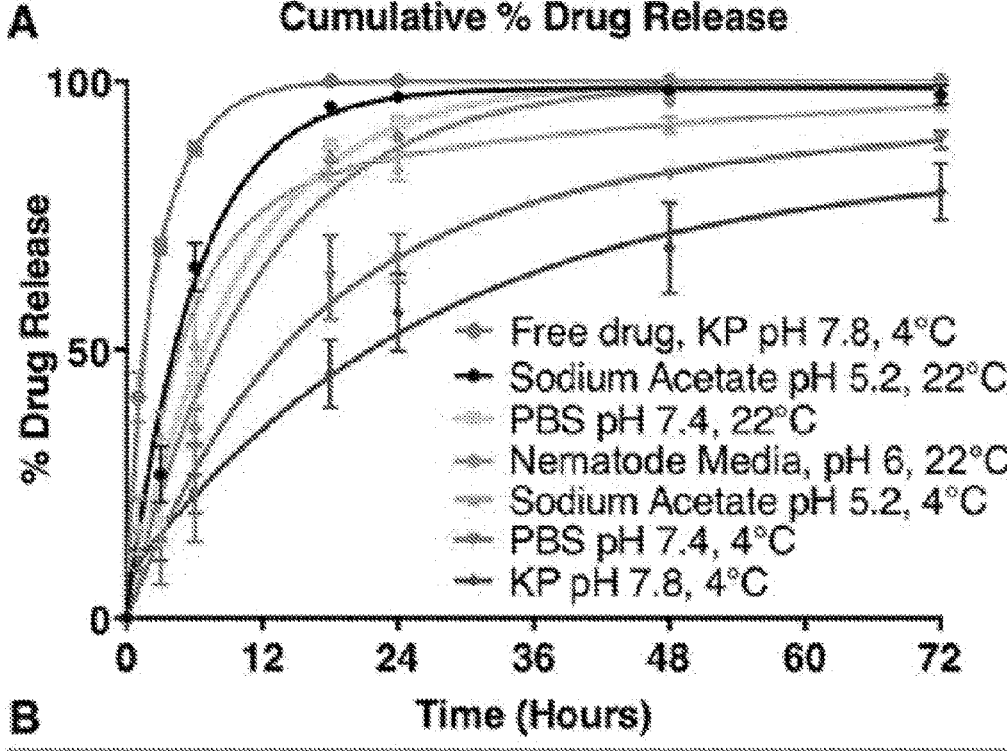
Free drug, KP pH 7.8, 4°C
Sodium Acetate pH 5.2, 22°C
PBS pH 7.4, 22°C
Nematode Media, pH 6, 22°C
Sodium Acetate pH 5.2, 4°C
PBS pH 7.4, 4°C
KP pH 7.8, 4°C
B
| Sample Name | pH | Temperature | Legend | Drug Release Half Life (hours) |
|---|---|---|---|---|
| Free Drug, KP | 7.8 | 4°C | | 1.6 |
| Sodium Acetate | 5.2 | 22°C | | 5 |
| PBS | 7.4 | 22°C | | 7.3 |
| Nematode Media | 6 | 22°C | | 7.9 |
| Sodium Acetate | 5.2 | 4°C | | 4.8 |
| PBS | 7.4 | 4°C | | 11.3 |
| KP | 7.8 | 4°C | | 13 |
Figs. 4A-B

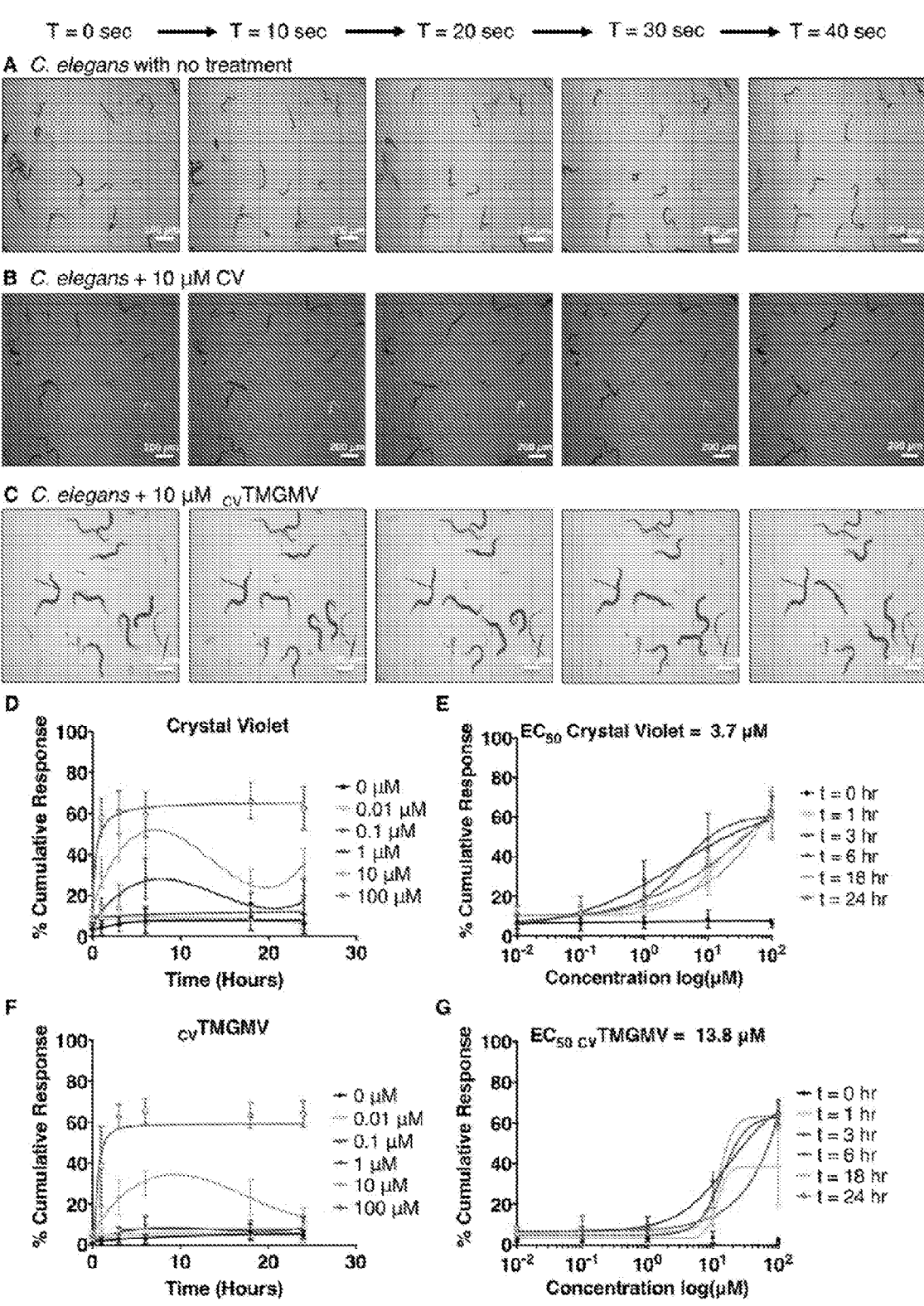
Figs. 5A-G

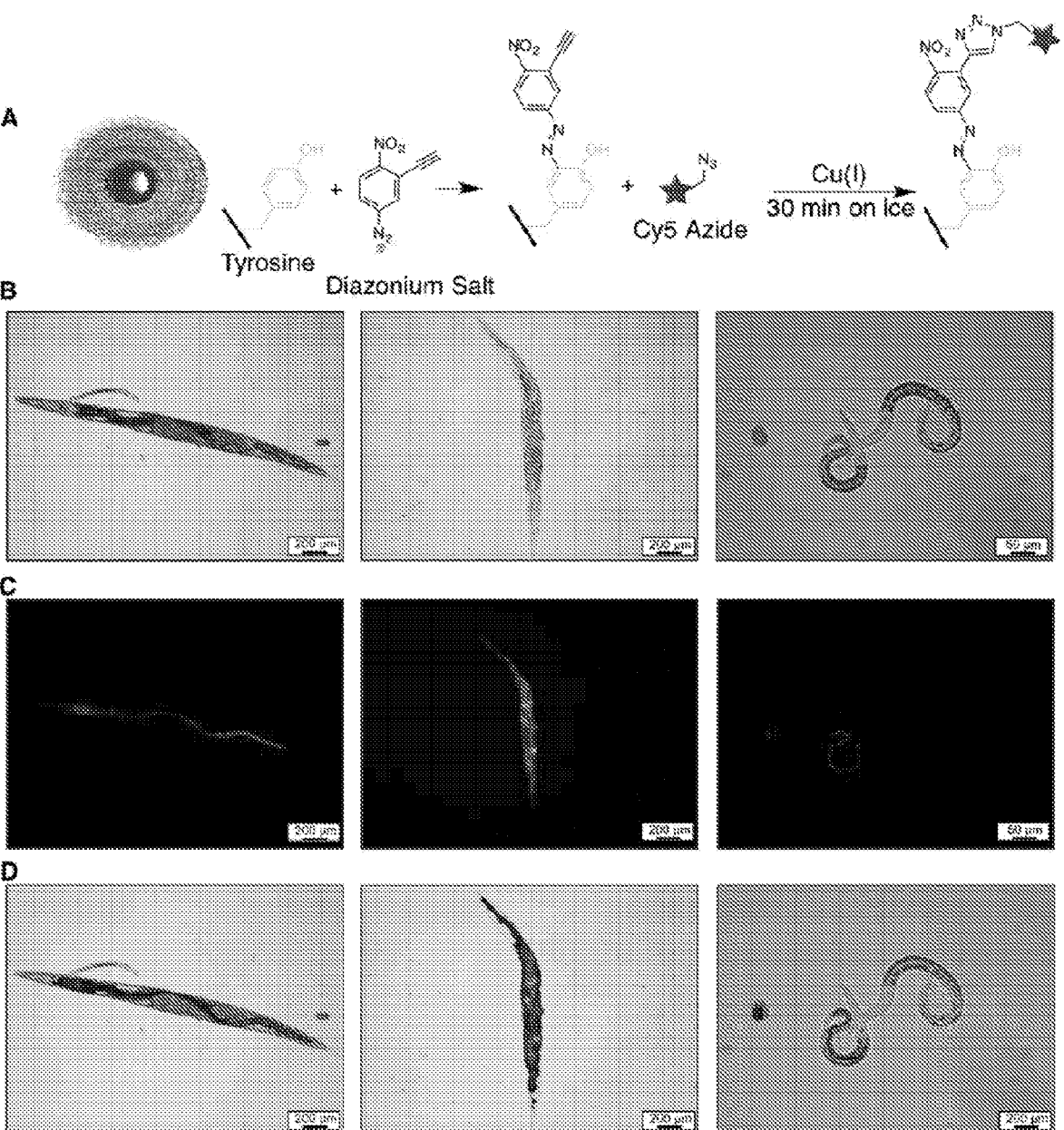
Figs. 6A-D

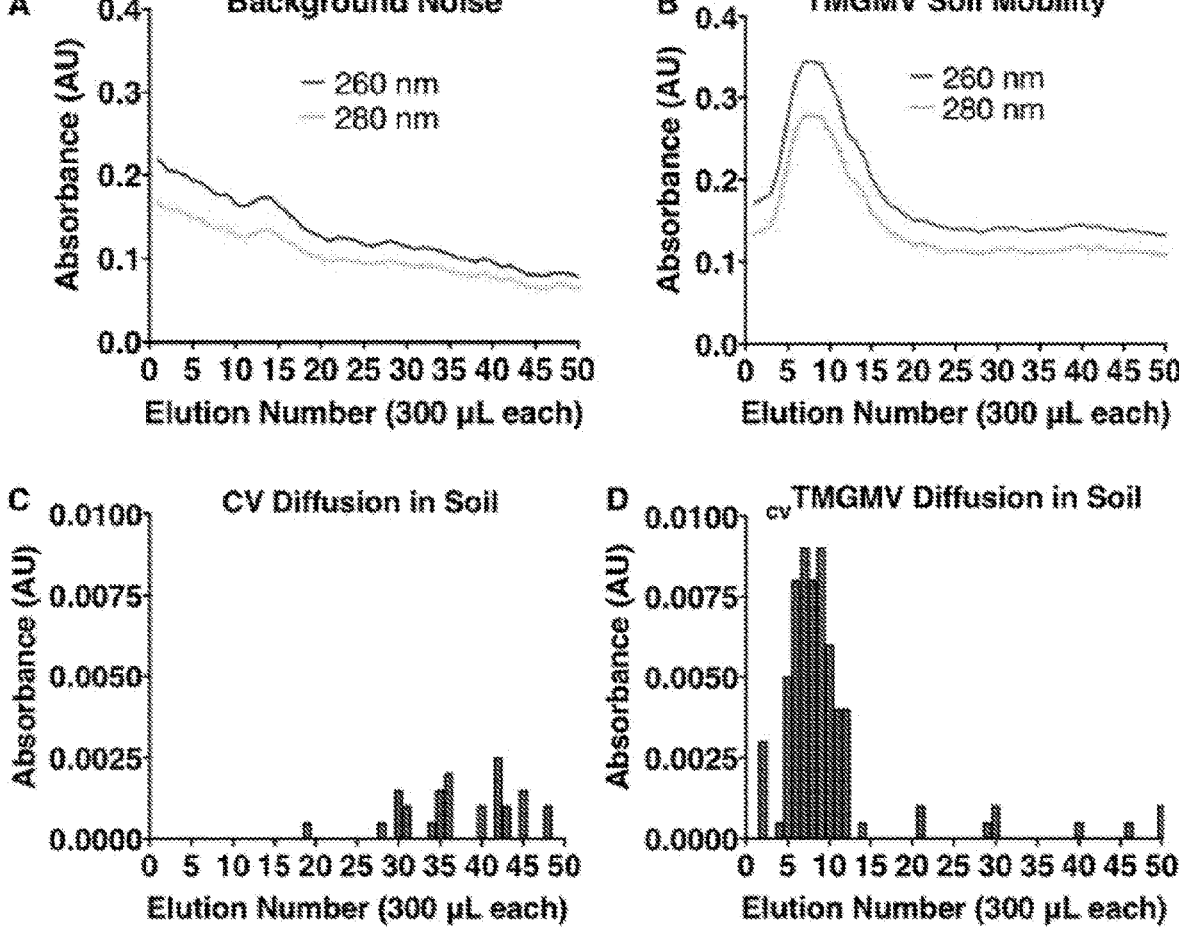
Figs. 7A-D

ROD-SHAPED PLANT VIRAL NANOPARTICLES OR VIRUS-LIKE PARTICLES FOR AGRICULTURAL APPLICATIONS

RELATED APPLICATION

This application claims priority from U.S. Provisional Application No. 62/345,212, filed Jun. 3, 2016, the subject matter of which is incorporated herein by reference in its entirety.

GOVERNMENT FUNDING

This invention was made with government support under Grant Nos. DMR1452257 awarded by The National Science Foundation. The United States government has certain rights to the invention.

BACKGROUND

Plant parasites are a major burden to the global agricultural industry. Among them, the United States Department of Agriculture (USDA) has highlighted several species of insects and worms (i.e., moths, beetles, fruit flies, grasshoppers, ants, and nematodes) as the most common and devastating parasites. Plant parasites either directly injure crops by feeding on them or indirectly cause injury through the transmission of bacteria, viruses, and fungi.

Endoparasitic plant nematodes feed on the crop roots, causing distinctive root swellings commonly referred to as galls. Gall formation impairs the root conduction of water and growth nutrients into the rest of the plant, resulting in lower crop yields. In addition, galls often promote crack damages in the roots and increase the plant vulnerability to secondary infections.

The root-knot *Meloidogyne* spp, the potato cyst *Globodera* spp, and the soybean cyst *Heterodera glycines* are the most damaging and widely spread plant parasitic nematodes. Combined they can infect more than 3000 plant species, including bananas, corn, cotton, potatoes, lettuce, and tomatoes. While crop nematode infestation is relatively easy to diagnose (e.g., dig up a few plants and examine the roots for gall formation), treatment options are limited.

In most countries, crop rotation is frequently employed to selectively control plant parasitic nematode infestations. Nonetheless, the wide host range of root-knot nematodes limits the choice of alternate crops to a few species, yielding little to no revenue. Genetically modified crops resistant to nematodes are an economically and environmentally viable alternative. Unfortunately, genetic resistance to plant parasitic nematodes is selective to specific nematode species, limited to a few crops, and takes years to engineer.

While these aforementioned control strategies can reduce the burden of plant parasitic nematodes on most crops, their efficacy and economic benefits are no match to the use of nematicides. The first generation of nematicides rely on highly toxic and volatile fumigants, such as methyl bromide, but their use has declined due to environmental (e g, thinning of the ozone layer and undiscriminating killing of animals such as bees) and health (e.g., reproductive sterility and cancer) concerns. Alternatively, nonfumigant nematicides, such as organophosphates, carbamates, and bionematicides, have been employed. Their efficacy, however, is limited by their ability to diffuse through soil, which is dependent on the amount of organic matter, moisture, and the soil structure (e.g., grain size and soil density). To be effective, nonfumigant nematicides must persist long enough and in concentrations equivalent to the nematode-lethal dose at root level. Extended persistence in such doses increases the risk of chemical contamination of crops, soil, and groundwater. Therefore, there is a critical need to resolve soil mobility issues of nematicides to enhance their agrochemical efficacy, reduce their indiscriminate use, and ensure their safe application.

SUMMARY

Embodiments described herein relate to rod-shaped viral nanoparticles (VNPs) or viruses, and/or virus-like particles (VLPs) thereof that are as used as carriers to deliver at least one agrochemical agent or ingredient in a controlled and targeted manner for agricultural applications. Rod-shaped plant VNPs or VLPs can provide an economically and environmentally viable alternative to conventional synthetic nanoparticles. Plant VNPs and their VLPs can be produced in large quantities in a short time for a relatively low price. In addition, plant VNPs and their VLPs are exceptionally robust to the harsh environment of crop fields, biodegradable, as well as biocompatible and noninfectious, making them safe to use on industrial crops.

In some embodiments, an agricultural composition can include a plurality of rod-shaped VNPs and/or VLPs and at least one agrochemical agent that is conjugated to and/or loaded on and/or within the VNPs and/or VLPs. The rod shaped VNPs and/or VLPs can have an exterior surface and an interior surface that extend from a first end to a second of the rod-shaped VNPs and/or VLPs. The interior surface can define a channel that extends through rod-shaped VNP from the first end to the second end. The channel includes the viral genome (VNP) or lacks the viral genome (VLP). The agrochemical agent can be conjugated to an interior and/or exterior surface of the VNPs and/or VLPs.

In some embodiments, the VNPs and/or VLPs include Virgaviridae virus particles. In other embodiments, the VNPs and/or VLPs include at least one VNP and/or VLP of the Tobamovirus species. Particular examples include, but are not limited to, tobacco mild green mosaic virus, and tobacco mosaic virus and VLPs thereof.

In other embodiments, the agrochemical agent can be covalently or noncovalently coupled and/or conjugated to the VNPs and/or VLPs. In one example, positively charged agrochemical agents can be non-covalently loaded onto negatively charged interior or exterior surfaces of the rod-shaped VNPs and/or VLPs by electrostatic interactions between the positively charged agrochemical and negatively charged amino acid residues, charged groups, polymers, and/or dendrimers on the interior and exterior surface of the rod-shaped VNPs and/or VLPs. In another example, agrochemical agents can be covalently bound to chemically modified amino acid residues on the interior or exterior surface of the rod-shaped VNPs and/or VLPs.

The agrochemical agent conjugated to the interior and/or exterior surface of the rod-shaped VNP can be selected from the group consisting of nematicides, fungicides, herbicides, pesticides, acaricides, rodenticides, plant growth regulators, nutrients, pest repellents, and combinations thereof.

In some embodiments, the agricultural composition can be formulated as an emulsion, suspension, dispersion, or the like to facilitate delivery of the rod-shaped VNPs and/or VLPs to a pest, plant, plant organ, plant propagation material, or a surrounding area thereof.

Other embodiments described herein relate to a method of treating a plant. The method can include applying an agricultural composition as described herein to the plant in a treatment effective amount. Such plants are generally angiosperms or gymnosperms, and in some embodiments are monocots or dicots. In some embodiments, the plant is wheat, corn (maize), soybean, cotton, cassava, potato, sweet potato, bananas, citrus, strawberries, tomato, coffee, carrots, peppers, turf grass, or greenhouse ornamentals, taro, oats, barley, cereal rye, breadfruit, pea, rice, yams, garbanzo (chickpea), Jerusalem artichoke, or lentil.

In some embodiments, the plant may be is in the form of a plant part, such as leaves, flowers, stems, roots, tubers, fruits, and seeds.

In other embodiments, the composition is applied in an amount effective to combat nematode parasitism on said plant.

A further embodiment described herein is a plant having an agriculturalcomposition as described herein contacted thereto (e.g., the agricultural composition coated thereon (such as a seed coating), or the plant at least partially embedded therein). Such plants are, in general, angiosperms or gymnosperms, and in some embodiments monocots or dicots. Such plants may be in the form of a plant part such as leaves, flowers, stems, roots, tubers, fruits, and seeds. In some embodiments, the plant is wheat, corn (maize), soybean, cotton, cassava, potato, sweet potato, bananas, citrus, strawberries, tomato, coffee, carrots, peppers, turf grass, or greenhouse ornamentals.

In some embodiments, the rod-shaped VNPs and/or VLPs loaded with the agrochemical agent can have a greater soil mobility than the agrochemical agent alone. This can provide agrochemical agent loaded rod-shaped VNPs and/or VLPs with enhanced penetration through soil to reach pests, such as nematodes, that feed on the roots of plants.

BRIEF DESCRIPTION OF THE DRAWINGS

FIGS. 1(A-F) illustrate schematic drawings showing the structure of TMGMV. (A) Depiction of a single CP of TMGMV in various orientations highlighting surface-exposed glutamic acid (Glu) and aspartic acid (Asp). Full-length TMGMV is formed by 2130 identical CP copies. (B) The cross-sectional orientation of the fully assembled TMGMV reveals the 4 nm-wide hollow channel of the 18 nm-wide cylindrical TMGMV. (C) Representation of a portion (300 CPs are depicted) of TMGMV in its longitudinal orientation; structural data indicate that Glu145 and Asp66 are solvent exposed on the exterior TMGMV surface. (D) Glu95 and Glu106 appear solvent exposed on the interior channel surface with Glu95 being more exposed than Glu106. (E, F) Coulombic surface coloring of the exterior and interior TMGMV surfaces.

FIGS. 2(A-C) illustrate schematic drawings showing $_{CV}$TMGMV conjugation and characterization. (A) Schematic of CV loading into TMGMV (shown in cross sectional orientation) and purification of $_{CV}$TMGMV samples prior to analysis. (B) Chemical modification of the carboxylate groups via EDC and click chemistry to prevent CV loading. (C) Schematic of unsuccessful CV loading into modified $_{Glu/Asp-Biotin}$TMGMV or $_{Glu/Asp/Alkyne}$TMGMV.

FIGS. 3(A-H) illustrate plots and images showing characterization of $_{CV}$TMGMV particles. (A) UV—vis spectra of $_{CV}$TMGMV. Each spectrum results from a different molar excess of CV:TMGMV. Spectra were normalized to the 260 nm wavelength peak. (B) Corresponding average number of CV molecules per TMGMV. (C) UV—vis spectra of $_{CV}$TMGMV and $_{Glu/Asp/EDC}$TMGMV+CV. (D) SDS-NuPAGE and Western blot of TMGMV and $_{Glu/Asp/Biotin}$TMGMV, confirming covalent binding of biotin to TMGMV proteins. (E) CV loading in $_{Glu/Asp/biotin}$TMGMV resulted in severe aggregation compared to unmodified TMGMV. (F) Size exclusion chromatography shows matched elution profiles of TMGMV and CVTMGMV. Both samples have an elution volume of 8 mL. RNA absorbs at 260 nm and protein at 280 nm. (G) TEM images of negatively stained (UAc) unmodified TMGMV and (H) CVTMGMV.

FIGS. 4(A-B) illustrate a plot and chart showing evaluation of CV drug release from TMGMV. (A) Cumulative percent release of free CV from $_{CV}$TMGMV in various buffer conditions over 72 h. Sample conditions were as follows: CV free drug diffusion in the absence of TMGMV in KP buffer (10 mM, pH 7.8, 4° C.), CV release from $_{CV}$TMGMV in sodium acetate buffer (10 mM, pH 5.2, 22° C.) (black) and 4° C. (orange)), CV release from CVTMGMV in PBS (10 mM, pH 7.4, 22° C.) (green) and 4° C. (red), CV release from $_{CV}$TMGMV KP buffer (10 mM, pH 7.8, 4° C.) (blue), and CV release from $_{CV}$TMGMV in nematode media, pH 6, 22° C. (pink). (B) CV drug release half-life in the corresponding buffer conditions.

FIGS. 5(A-G) illustrate images and plots showing C. elegans motility assay. (A) Time lapse imaging of C. elegans in the absence of CV treatment. Images shown were taken at 10 s intervals. Five nematodes were pseudocolored (dark blue, sky blue, red, pink, and yellow) to demonstrate their movement over time. (B) The five pseudocolored nematodes in the presence of 10 µM of free CV and (C) 10 µM of CV loaded in CVTMGMV have very limited to no movement. Some nonpseudocolored nematodes are still mobile. (D) Cumulative percent response to free CV (C. elegans with no or with impaired mobility) over 24 h as a function of time and (E) CV concentration. (F) Cumulative percent response to CVTMGMV as a function of time and (G) CV concentration.

FIGS. 6(A-D) illustrate a schematic illustration and images showing C. elegans ingestion of TMGMV. (A) Schematic of Cy5 conjugation to the surface exposed Tyr2 groups (yellow) on the surface of TMGMV. (B) Bright-field microscopy of C. elegans incubated with $_{Cy5}$TMGMV for 3 h. (C) Corresponding fluorescent images. (D) Brightfield and fluorescent images were merged to confirm colocation.

FIGS. 7(A-D) illustrate plots showing soil mobility of $_{CV}$TMGMV and free CV. UV—vis spectrum at λ260 (RNA) and λ280 (CPs) from 50 elution fractions collected from the leaching of (A) CV and (B) $_{CV}$TMGMV in 4 cm of top soil. The corresponding absorbance spectrum of CV (λ590) was also recorded for the elution of (C) CV alone and (D) $_{CV}$TMGMV.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this invention belongs.

The term "about" as used herein when referring to a measurable value such as an amount, a temporal duration, and the like, is meant to encompass variations of .+−0.20% or 110%, more preferably .+−0.5%, even more preferably .+−0.1%, and still more preferably .+−0.0.1% from the specified value, as such variations are appropriate to perform the disclosed methods.

The term "effective amount" refers to an amount of an agent that is sufficient to provide a desired effect. An effective amount in any individual case may be determined by one of ordinary skill in the art using routine experimentation.

The term "nematode" as used herein includes, but is not limited to, plant-parasitic nematodes such as *Meloidogyne* root knot nematodes, *Globodera* and *Heterodera* cyst nematodes, *Pratylenchus* lesion nematodes, *Dietylenchus* stem and bulb nematodes, *Tylenchulus* citrus nematodes, *Xiphinema* dagger nematodes, *Radopholus* burrowing nematodes, *Rotylenchulus* reniform nematodes, *Helicotylenchus* spiral nematodes, and *Belonolaimus* sting nematodes.

The term "plant" as used herein generally refers to vascular plants. "Plant" refers to both whole plants and parts thereof, such as stems, leaves, flowers, fruit, tubers, seeds, roots, etc.

The term "plant propagation material" is understood to denote all the generative parts of the plant, such as seeds, which can be used for the multiplication of the latter and vegetative plant materials such as cuttings and tubers (for example, potatoes). Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Embodiments described herein relate to rod-shaped viral nanoparticles (VNPs) or virus and/or virus-like particles (VLPs) thereof that are as used as carriers to deliver agrochemical agents or ingredients in a controlled and targeted manner for agricultural applications. Rod-shaped plant VNPs and/or VLPs can provide an economically and environmentally viable alternative to conventional synthetic nanoparticles. Plant VNPs and/or VLPs can be produced in large quantities in a short time for a relatively low price. In addition, plant VNPs and/or VLPs are exceptionally robust to the harsh environment of crop fields, biodegradable, as well as biocompatible and noninfectious, making them safe to use on industrial crops. Advantageously, rod-shaped VNPs and/or VLPs, in comparison to VNPs and/or VLPs having other geometries, such as spherical or icosahedral VNPs and/or VLPs, can provide higher loading and delivery of agrochemical agents as well as enhanced soil mobility for delivery of the agrochemical agents to plant roots.

The rod-shaped VNPs and/or VLPs that are used as carriers to deliver the agrochemical agents can have an exterior surface and an interior surface that extend from a first end to a second of the rod-shaped VNP and/or VLP. The interior surface can define a central hollow channel that extends through rod-shaped VNP and/or VLP from the first end to the second end. The channel can include the viral genome (e.g., VNP) or be substantially free of or lack the viral genome (e.g., VLP). The agrochemical agent can be conjugated to and/or loaded on the interior and/or exterior surface of the rod-shaped VNP and/or VLP to provide an agricultural composition which can be readily delivered to a pest, plant, part of plant, plant organ, plant propagation material, and/or surrounding area thereof.

The rod-shaped plant viruses used as the rod-shaped VNPs and/or VLPs can be shaped as a rigid helical rod with a helical symmetry. Rod-shaped plant VNPs and/or VLPs are distinguished from filamentous plant virus particles as being inflexible, shorter, and thicker in diameter. For example, Virgaviridae viruses have a length of about 200 to about 400 nm, and a diameter of about 15-25 nm. Virgaviridae viruses have other characteristics, such as having a single-stranded RNA positive sense genome with a 3'-tRNA like structure and no polyA tail, and coat proteins of 19-24 kilodaltons.

The rod-shaped plant virus can belong to a specific virus family, genus, or species. In some embodiments, the rod-shaped plant virus belongs to the Virgaviridae family. The Virgaviridae family includes the genus *Furovirus, Hordevirus, Pecluvirus, Pomovirus, Tobamovirus*, and *Tobravirus*. In other embodiments, the rod-shaped plant virus belongs to the genus Tobamovirus. In further embodiments, the rod-shaped plant virus belongs to the tobacco mild green mosaic virus (TMGMV) species or tobacco mosaic virus species.

In some embodiments, the rod-shaped VNP and/or VLPs formed thereof used in the agricultural composition is TMGMV. TMGMV self assembles into a 300×18 nm rod-shaped virus with a 4 nm wide hollow interior channel Similar to tobacco mosaic virus (TMV), TMGMV includes a single copy of coat protein (CP) arranged helically around a single stranded RNA genome. Advantageously, TMGMV also has a high surface area ($3.6×10^{-14}$ m$^2$ on the exterior and $7.6×10^{-15}$ m$^2$ on the interior) compared to icosahedral viruses that can allow for higher payload delivery of agrochemical agents.

TMGMV is commercially available under the tradename Solvinix from BioProdex. It is currently EPA approved as an herbicide in the state of Florida for the treatment of the invasive weed tropical soda apple. Advantageously, TMGMV is not transmitted by insects, pollen, or other vectors; it is not seed borne and cannot self-disseminate. While TMGMV is capable of infecting solanaceous plants (e.g., tomatoes, chili peppers, and eggplants), TMGMV is unable to penetrate and infect healthy plants in the absence of a lesion wound. Furthermore, Solvinix was tested on 435 plants representing 311 species, among which only 8% of plants were killed. TMGMV can, therefore, be used as a carrier for an agrochemical agent and be applied for agricultural applications with little to no risk to the environment or the crop itself.

The at least one agrochemical agent, which can be conjugated to and/or loaded on the interior and/or exterior surface of the rod-shaped VNP and/or VLPs (e.g., TMGMV), can include any agrochemical agent that covalently or non-covalently conjugated to the rod-shaped VNPs and/or VLPs and/or that can be suitable for agricultural applications. Examples of agrochemical agents that can be covalently or non-covalently conjugated to the rod-shaped VNPs and/or VLPs include, but are not limited to, pesticides (e.g., nematicides, insecticides, acaricides, fungicides, herbicides, etc.) plant growth regulators, nutrients, pest repellents, and the like. Examples of agrochemical agents, which can be used with rod-shaped VNPs and/or VLPs described herein, are described in U.S. Patent Application No. 2011/0200571; U.S. Pat. Nos. 8,119,150; 7,836,630; 6,776,996; 6,660,690; 6,638,994; and 6,602,82, the disclosures of which agrochemical agents found therein are incorporated by reference herein in their entirety. Particular examples include but are not limited to those discussed in greater detail below.

In some embodiments, the agrochemical agent can be a nematicide. Examples of nematicides that can be conjugated to and/or loaded on the interior and/or exterior surface of the rod-shaped VNP include, but are not limited to, anthelmintics, such as crystal violet (hexamethyl parparosaniline chloride), antibiotic nematicides, such as abamectin; carbamate nematicides, such as benomyl, carbofuran, carbosulfan, and cleothocard; oxime carbamate nematicides, such as alany-carb, aldicarb, aldoxycarb, oxamyl; organophosphorous nematicides, such as diamidafos, fenamiphos, fosthietan, phosphamidon, cadusafos, chlorpyrifos, dichlofenthion, dimethoate, ethoprophos, fensulfothion, fosthiazate, hetero-phos, isamidofos, isazofos, methomyl, phorate, phospho-carb, terbufos, thiodicarb, thionazin, triazophos, imicyafos, and mecarphon. Other compounds with nematicidal activity include acetoprole, benclothiaz, chloropicrin, dazomet, DB CP, DCIP, 1,2-dichloropropane, 1,3-dichloropropene, fur-fural, iodomethane, metam, methyl bromide, methyl isoth-iocyanate, and xylenols.

In other embodiments, the agrochemical agent can be a fungicide. Examples of fungicides that can be conjugated to and/or loaded on the interior and/or exterior surface of the rod-shaped VNP include, but are not limited to, aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, boscalid, bromuconazole, bupirimate, buthiobate, calcium polysulphide, capsimycin, captafol, captan, carbendazim, carboxin, carvon, quinome-thionate, chiobenthiazone, chlorfenazol, chloroneb, chlo-ropicrin, chlorothalonil, chlozolinate, clozylacon, cufraneb, cymoxanil, cyproconazole, cyprodinil, cyprofuram, debac-arb, dichlorophen, diclobutrazole, diclofluanid, diclomezine, dicloran, diethofencarb, difenoconazole, dimethirimol, dimethomorph, dimoxystrobin, diniconazole, diniconazole-M, dinocap, diphenylamine, dipyrithione, ditalimfos, dithi-anon, dodemorph, dodine, drazoxolon, edifenphos, epoxi-conazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, flumetover, fluoromide, fluquinconazole, flurprimidol, flusi-lazole, flusulfamide, flutolanil, flutriafol, folpet, fosetyl-aluminium, fosetyl-sodium, fthalide, fuberidazole, fural-axyl, furametpyr, furcarbonil, furconazole, furconazole-cis, furmecyclox, guazatine, hexachlorobenzene, hexaconazole, hymexazole, imazalil, imibenconazole, iminoctadine, imi-noctadine albesilate, iminoctadine triacetate, iodocarb, ipconazole, iprobenfos (IBP), iprodione, irumamycin, iso-prothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamo-carb, oxolinic acid, oxycarboxim, oxyfenthiin, paclobutra-zole, pefurazoate, penconazole, pencycuron, phosdiphen, pimaricin, piperalin, polyoxin, polyoxorim, probenazole, prochloraz, procymidone, propamocarb, propanosine-so-dium, propiconazole, propineb, prothiocinazole, pyra-clostrobin, pyrazophos, pyrifenox, pyrimethanil, pyro-quilon, pyroxyfur, quinconazole, quintozene (PCNB), sulphur and sulphur preparations, tebuconazole, tecloftalam, tecnazene, tetcyclasis, tetraconazole, thiabendazole, thicy-ofen, thifluzamide, thiophanate-methyl, thiram, tioxymid, tolclofos-methyl, tolylfluanid, triadimefon, triadimenol, tri-azbutil, triazoxide, trichlamide, tricyclazole, tridemorph, trifloxystrobin, triflumizole, triforine, triticonazole, unicona-zole, validamycin A, vinclozolin, viniconazole, zarilamide, zineb, ziram and also Dagger G, OK-8705, OK-8801, .alpha.-(1,1-dimethylethyl)-.beta.-(2-phenoxyethyl)-1H-1,2, 4-tri-azole-1-e-thanol, .alpha.-(2,4-dichlorophenyl)-.beta.-fluoro-.beta.-propyl-1H-1,2,4-triazol-e-1-ethanol, .alpha.-(2,4-dichlorophenyl)-.beta.-methoxy-.alpha.-methyl-1H-1, 2,4-triaz-ole-1-ethanol, .alpha.-(5-methyl-1,3-dioxan-5-yl)-. beta.-[[4-(trifluoromethyl)-phenyl]-m-ethylene]-1H-1,2,4-triazole-1-ethanol, (5RS,6RS)-6-hydroxy-2,2,7,7-tetram-ethyl-5-(1H-1,2,4-triazol-1-yl)-3-octan- -one, (E)-.alpha.-(methoxyimino)-N-methyl-2-phenoxy-phenylacetamide, 1-isopropyl 1-{2-methyl-1-[[[1-(4-methylphenyl)-ethyl]-amino]-carbonyl]-prop-yl}carbama-te, 1-(2,4-dichlorophe-nyl)-2-(1H-1,2,4-triazol-1-yl)-ethanone-O-(phenylmet-hyl-)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazo-1e-5-carboxanilide, 2,2-dichloro-N-[1-(4-chloro-phenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-di-chloro-N-[[4-(trifluoromethyl)-phenyl]-methyl]-benzamide, 2-(2,3,3-triiodo-2-propenyl)-2H-tetrazole, 2-[(1-methyl-ethyl)-sulphonyl]-5-(trichloromethyl)-1,3,4-thiadiazole, 2-[[6-deoxy-4-O-(4-O-methyl-D-glycopyranosyl)-.alpha.-D-glucopyran-osyl]-amino]-4-methoxy-1H-pyrrolo[2,3-d] pyrimidine-5-carbonitrile, 2-aminobutane, 2-bromo-2-(bro-momethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dim-ethylethyl)-N-ethyl-N-propyl-1,4-dioxaspiro[4,5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2, 4-triazol-1-yl)-cycloheptanol, cis-4-[3-[4-(1,1-dimethylpropyl)-phenyl-2-methylpropyl]-2,6-dimethyl-morp-holine hydrochloride, ethyl [(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alani-nate, N-(2,3-dichloro-4-hydroxyphenyl)-1-methyl-cyclo-hexanecarboxamide, N-(2,6-dimethylphenyl)-2-methoxy-N-(tetrahydro-2-oxo-3-furanyl)-acetamide-dimethylphenyl)-2-methoxy-N-(tetrahydro-2-oxo-3-thienyl)-acetamid-e, N-(2-chloro-4-nitrophenyl)-4-methyl-3-nitro-benzenesulphonamide, N-(4-cyclohexylphenyl)-1,4, 5,6-tetrahydro-2-pyrimidinamine, N-(4-hexylphenyl)-1,4,5, 6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloro acetyl)-amino]-ethyl]-benzamide, N-[3-chloro-4,5-bis(2- propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, and Trilex-Yield Shield (Bayer CropScience) alone or in combination.

In still other embodiments, the agrochemical agent can be an insecticide. Examples of insecticides that can be conjugated to and/or loaded on the interior and/or exterior surface of the rod-shaped VNP and/or VLP include, but are not limited to, neonicotinoid insecticides such 1-(6-chloro-3-pyridylmethyl)-N-nitroimidazolidin-2-ylideneamine (imidacloprid), 3-(6-chloro-3-pyridylmethyl)-1,3-thiazolidin-2-ylidene cyanamide (thiacloprid), 1-(2-chloro-1,3-thiazol-5-ylmethyl)-3-methyl-2-nitroguanidine (clothianidin), nitempyran, $N^1$-[(6-chloro-3-pyridyl)methyl]-N.sup.2-cyano-$N^1$-methylacetamidine (acetamiprid), 3-(2-chloro-1, 3-thiazol-5-ylmethyl)-5-methyl-1,3,5-oxadiazinan-4-ylidene(-nitro)amine (thiamethoxam) and 1-methyl-2-nitro-3-(tetrahydro-3-furylmethyl) guanidine (dinotefuran).

In other embodiments, the agrochemical agent can be a herbicide. Examples of herbicides that can be conjugated to and/or loaded on the interior and/or exterior surface of the rod-shaped VNP include, but are not limited to: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; aryl-alanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metfluorazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron, noruron and saflufenacil; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, indaziflam, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

In yet other embodiments, the agrochemical agent can be a plant growth regulator. Examples of plant growth regulators that can be conjugated to and/or loaded on the interior and/or exterior surface of the rod-shaped VNP and/or VLP include but not limited to azoles (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide), and those described in PCT Patent Application WO 2011063947.

The agrochemical agents can be conjugated to and/or loaded on the interior and/or exterior surface of the rod-shaped VNPs and/or VLPs by any suitable technique. The term "conjugating" when made in reference to an agrochemical agent and a rod-shaped VNP and/or VLP as used herein includes covalently or non-covalently linking, attaching, binding, and/or coupling the agent to the VNPs and/or VLPs. The agrochemical agent can be covalently or non-covalently linked to the interior or the exterior surfaces of the rod-shaped VNPs and/or VLPs or to both the interior and the exterior surface of the rod-shaped VNPs and/or VLPs.

The location of the agrochemical agent on the interior or exterior can be governed by the amino acids of the viral coat protein that are selected as reactive sites for covalent linking or the electrostatic properties of the exposed amino acid residues of the interior and/or exterior surface for non-covalent linking.

In some embodiments, agrochemical agents described herein can be covalently bound to chemically modified exposed amino acid residues on the interior and/or exterior surface of the rod-shaped VNPs and/or VLPs, such as carboxylate groups of exposed glutamic acid and aspartic acid residues on the interior and/or exterior surface of the rod-shaped VNPs and/or VLPs. The carboxylate groups of these amino acids also present attractive targets for functionalization using carbodiimide activated linker molecules. Exposed cysteines and lysine residues can also be present which facilitate chemical coupling via thiol-selective chemistry (e.g., maleimide-activated compounds. Further, exposed tyrosines on the on the interior and/or exterior surface of the rod-shaped VNPs and/or VLPs can be modified using diazonium coupling reactions. In addition, genetic modification can be applied to introduce any desired functional residue, including non-natural amino acids, e.g., alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

By way of example, 1-Ethyl-3-(3-dimethylaminopropyl) carbodiimide (EDC) coupling can used to chemically modifiy surface exposed glutamic and/or aspartic residues of the rod-shaped VNPs and/or VLPs to introduce alkyne ligands. The introduced alkyne ligands can then be reacted with azide groups attached to agrochemical agents using Cu(I)-catalyzed alkyne-azide cycloaddition (click chemistry).

In other embodiments, a suitable chemical binder group can be used. A binder group can serve to increase the chemical reactivity of a substituent on either the agrochemical agent or rod-shaped VNP and/or VLP, and thus increase the coupling efficiency. Examples of binder chemistries include maleimidyl binders, which can be used to bind to thiol groups, isothiocyanate and succinimidyl (e.g., N-hydroxysuccinimidyl (NHS)) binders, which can bind to free amine groups, diazonium which can be used to bind to phenol, and amines, which can be used to bind with free acids such as carboxylate groups using carbodiimide activation.

Useful functional groups present on exposed viral coat proteins of the rod-shaped VNPs and/or VLPs based on the particular amino acids present, and additional groups can be designed into recombinant viral coat proteins. It will be evident to those skilled in the art that a variety of bifunctional or polyfunctional reagents, both homo- and heterofunctional (such as those described in the catalog of the Pierce Chemical Co., Rockford, Ill.), can be employed as a binder group. Coupling can be effected, for example, through amino groups, carboxyl groups, sulfhydryl groups or oxidized carbohydrate residues.

Other types of binding chemistries are also available. For example, methods for conjugating polysaccharides to peptides are exemplified by, but not limited to coupling via alpha- or epsilon-amino groups to NaIO$_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide binder wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, rather than covalent attachment, at least one agrochemical agent described herein can be loaded on an exterior and/or interior surface of the rod-shaped VNPs and/or VLPs virus in a non-covalent manner by associating them with the rod-shaped VNPs and/or VLPs. The agrochemical agent can associate with the rod-shaped VNPs as a result of the affinity of the agrochemical agent to an exposed chemical group of the amino residue of the coat protein. Affinity is the tendency of a compound to naturally associate with another object. Affinity is influenced by non-covalent intermolecular interactions between the compound and the object, such as hydrogen bonding, electrostatic interactions, hydrophobic interactions, and Van der Waals forces.

In one example, positively charged agrochemical agents can have an affinity via electrostatic interactions to negatively charged interior or exterior surfaces of the rod-shaped VNPs and/or VLPs. The negatively charged interior or exterior surfaces can be provided by negatively charged amino acid residues, charged groups, polymers, and/or dendrimers on the interior and/or exterior surface of the rod-shaped VNPs and/or VLPs that are intrinsic to the VNPs and/or VLPs and/or provide by chemical modification and/or genetic addition to the VNPs and/or VLPs. By way of example, carboxylate groups of exposed aspartic acid and glutamic acid residues on the interior and exterior surface of the rod-shaped VNPs and/or VLPs can provide a negatively charged group that can interact electrostatically with the positively charged agrochemical agent.

It will be appreciated that the affinity of agrochemical agent for the interior and/or exterior surface of the rod-shaped VNP and/or VLP can be readily determined. For example gel mobility shift assays, crosslinking assays, optical absorbance and fluorescence assays, calorimetric assays, and/or surface Plasmon resonance assays to determine the association and dissociation kinetics and affinities of agrochemical agents for the rod-shaped VNPs and/or VLPs. Furthermore, any agrochemical agent exhibiting low affinity can be readily modified with a small, positively charged tag to bind to rod-shaped VNP and/or VLP.

In some embodiments, positively charged agrochemical agents can be non-covalently loaded onto negatively charged interior or exterior surfaces of the rod-shaped VNPs and/or VLPs by electrostatic interactions in a reversible manner, in order to facilitate release of the agrochemical agents from the rod-shaped VNPs and/or VLPs to a pest, plant, part of plant, plant organ, plant propagation material, and/or surrounding area thereof. The release rate of the agrochemical agent from the rod-shaped VNPs and/or VLPs can be controlled and be dependent on the pH of the microenvironment to which the agrochemical composition described herein is administered. Advantageously, administration of the agrochemical composition to soils having lower pH can promote more ready diffusion of the positively charged non-covalently loaded agrochemical agents from the rod-shaped VNPs and/or VLPs. As the pH of the soil decreases, a larger number of carboxylate groups can become protonated and carry a net neutral charge that can no longer interact with positively charged agrochemical agents allowing the positively charged agrochemical agents to diffuse from the rod-shaped VNPs and/or VLPs to the soil.

In other embodiments, at least two different agrochemical agents can be loaded on and/or within separate rod-shaped VNPs and/or VLPs or the same rod-shaped VNPs and/or VLPs. The at least two different agrochemical agents can demonstrate synergistic activity compared to the activity of the individual ingredients in the combination. Each combination of agrochemical agents loaded on and/or within the rod-shaped VNPs and/or VLPs may have advantageous properties for protecting plants against, for example, (i) pathogenic, such as phytopathogenic, especially fungi, attack or infestation, which result in disease and damage to the plant and/or (ii) insect or nematode attack or damage; particularly in the instance of plants, the agricultural compositions can control or prevent the pest damage on a seed, or parts of plant, plant organs and/or plants. Further, a combination according to the invention, in the absence of pathogenic or insect and/or nematode pressure, may improve the growth of a plant.

Such properties are for example the synergistically enhanced actions of combinations compared to the individual ingredients of the combination of agrochemical agents, resulting in, for example, lower pathogenic pest damage, lower rates of application, or a longer duration of action. In the instance of agriculture, the enhanced actions may show an improvement in the growing characteristics of a plant by, for example, higher than expected control of the pest damage, or higher than expected yield, stand establishment, germination, etc.

The improvement in the growing (or growth) characteristics of a plant can manifest in a number of different ways, but will typically result in a better product of the plant. It can, for example, manifest in improving the yield and/or vigour of the plant or quality of the harvested product from the plant, which improvement may not be connected to the control of pests, such as fungi, insects and nematodes.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

Accordingly, in some embodiments a method of improving the growing characteristics of a plant can include applying to the plant, part of plant, and/or plant propagation material, a combination of agrochemical agents loaded on and/or within one or more rod-shaped VNPs, as defined in the first aspect, in any desired sequence or simultaneously, especially in the absence of pathogenic or pests pressure.

Combinations of the disclosure can be used in the agricultural sector and related fields of use for controlling or preventing damage by pests, such as insect, nematode and pathogen.

Combinations according to the present disclosure, especially those containing one or more pesticidal agents selected, independently from each other may be effective against pest control, such as control of pests selected from Nematoda, Insecta and Arachnida. In that instance, the combination can also be applied on the pest to control or prevent pest damage and protect the desired material (e.g., plant and part of plant) from pest damage.

Particular pests controlled by the compositions of the present technology include those from the class Nematoda, for example, the species of *Tylenchus* spp., *Atylenchus* spp., *Anguina* spp., *Rotylenchus* spp., *Criconema* spp., *Tylenchulus* spp., *Paratylenchus* spp., *Aphenlenchus* spp., *Bursaphelenchus* spp., *Paralongidorus* spp., *Trichodorus* spp., *Meloidogyne* spp. (for example, *Meloidogyne incoginita* and *Meloidogyne javanica*), *Heterodera* spp. (for example, *Heterodera glycines, Heterodera schachtii, Heterodora avenae* and *Heterodora trifolii*), *Globodera* spp. (for example, *Globodera rostochiensis*), *Radopholus* spp. (for example, *Radopholus similes*), *Rotylenchulus* spp., *Pratylenchus* spp. (for example, *Pratylenchus neglectans* and *Pratylenchus penetrans*), *Aphelenchoides* spp., *Helicotylenchus* spp., *Hoplolaimus* spp., *Paratrichodorus* spp., *Longidorus* spp., *Nacobbus* spp., *Subanguina* spp. *Belonolaimus* spp., *Criconemella* spp., *Criconemoides* spp. *Ditylenchus* spp., *Dolichodorus* spp., *Hemicriconemoides* spp., *Hemicycliophora* spp., *Hirschmaniella* spp., *Hypsoperine* spp., *Macroposthonia* spp., *Melinius* spp., *Punctodera* spp., *Quinisulcius* spp., *Scutellonema* spp., *Xiphinema* spp., and *Tylenchorhynchus* spp.

The combinations can offer opportunities to manage resistance in pests, for example, *Plutella* spp. as well as to proactively manage insecticide resistance in various pests.

In some embodiments, a combination agrochemical agents may also be effective for enhancing the plants' traits. Examples of enhanced plant traits include, but are not limited to, increased stem girth, change in leaf color, early flowering, synchronization in flowering, decrease in the lodging, control of the canopy size of a plant, delaying or eliminating tie-up of crops, increase in the disease resistance, enhancing the water utilization/improving the water use efficiency, including but not limited to decreasing the watering and/or less frequent watering (demonstrated by less wilting of the plant, the ability of the plant to rejuvenate following a suspension in watering), higher yield, higher quality/healthier plant appearance, greater transportability, decreasing the insect damage, and smaller plant canopies. Synchronized flowering is indicated by blooms materializing within 0.5 to 1 days of one another throughout the entire crop. Such a combination is particularly well suited for use for plants and propagation material thereof which are transplanted.

In an embodiment, further agent(s), such as active agrochemical agents or ingredient(s), can be used with each combination. Therefore, each of the combinations of the may be mixed with, for example, one or more other known pesticides, such as other fungicides, insecticides, nematicides, etc. The use of additional agents, such as other active ingredients, can be for reasons, for example, broader spectrum control (e.g., wider variety of pests, diseases, etc), lower rates, synergy and economy. A skilled person would understand that a single pesticidal active ingredient may have activity in more than one area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

In some embodiments, agricultural compositions including the agrochemical agent(s) loaded rod-shaped VNPs and/or VLPs described herein can be provided as suitable formulations, such as solutions, emulsions, wettable powders, suspensions, powders, dusts, pastes, soluble powders, granules, suspoemulsion concentrates, natural and synthetic materials impregnated with active compound, and ultrafine encapsulations in polymeric materials. These formulations can produced in the known manner, for example by mixing the active compound with extenders, that is, liquid solvents and/or solid carriers, optionally with the use of surfactants, that is, emulsifiers and/or dispersants and/or foam formers. Suitable extenders are, for example, water, polar and unpolar organic chemical liquids, for example from the classes of the aromatic and nonaromatic hydrocarbons (such as paraffins, alkylbenzenes, alkylnaphthalenes, chlorobenzenes), of the alcohols and polyols (which can optionally also be substituted, etherified and/or esterified), of the ketones (such as acetone, cyclohexanone), esters (including fats and oils) and (poly)ethers, of the unsubstituted and substituted amines, amides, lactams (such as N-alkylpyrrolidones) and lactones, the sulphones and sulphoxides (such as dimethyl sulphoxide).

In the case of the use of water as an extender, organic solvents can, for example, also be used as cosolvents. Liquid solvents which are suitable are mainly: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral oils and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and water.

Solid carriers which are suitable are for example, ammonium salts and ground natural minerals, such as kaolins, clays, talc, chalk, quartz, attapulgite, montmorillonite or diatomaceous earth, and ground synthetic minerals, such as highly-disperse silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersants are: for example lignin-sulphite waste liquors and methylcellulose.

Any plant genus or species can be used with the methods and agricultural compositions described herein, including, but not limited to, monocots and dicots. See, e.g., U.S. Pat. No. 8,080,647 (Pioneer Hi Bred). Examples of plant genuses and species include, but are not limited to, corn (*Zea mays*), *Brassica* spp. (e.g., *B. napus, B. rapa, B. juncea*), castor, palm, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp. such as lemon, lime, orange, tangelo, tangerine, etc.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), *Arabidopsis thaliana*, oats (*Avena* spp.), barley (*Hordeum* spp.), leguminous plants such as guar beans, locust bean, fenugreek, garden beans, cowpea, mungbean, fava bean, lentils, and chickpea, vegetables, ornamentals, grasses and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Pisium* spp., *Lathyrus* spp.), and *Cucumis* species such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include pines, for example, loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas fir (*Pseudotsuga menziesii*); Western hemlock (*Tsuga canadensis*), Sitka spruce (*Picea glauca*), redwood (*Sequoia sempervirens*), true firs such as silver fir (*Abies amabilis*) and balsam fir (*Abies balsamea*), and cedars such as Western red cedar (*Thuja plicata*) and Alaska yellow cedar (*Chamaecyparis nootkatensis*).

The agricultural compositions described herein may be applied to pests, plants, parts of plants, plant organs, plant propagation materials, and/or surrounding areas thereof directly or indirectly by any suitable technique, including but not limited to spraying, atomizing, dusting, scattering, coating or pouring, depending upon the particular plant or crop being treated.

In some embodiments, a seed can be coated with the agricultural compositions described herein, and/or soil can be treated with the agricultural compositions described herein. The seeds may be substantially uniformly coated with one or more layers of the agricultural composition, concurrently or sequentially and one or more optional compounds using conventional methods of mixing, spraying or a combination thereof. Application is generally done using specifically designed and manufactured equipment that accurately, safely, and efficiently applies seed treatment products to seeds. Such equipment uses various types of coating technology such as rotary coaters, drum coaters, fluidized bed techniques, spouted beds, rotary mists or a combination thereof. In one embodiment, application is done via either a spinning "atomizer" disk or a spray nozzle which evenly distributes the seed treatment onto the seed as it moves through the spray pattern. The seed may then be mixed or tumbled for an additional period of time to achieve additional treatment distribution and drying. The seeds can be primed or unprimed before coating with the inventive compositions to increase the uniformity of germination and emergence. In an alternative embodiment, a dry powder composition can be metered onto the moving seed.

The seeds may be coated via a continuous or batch coating process. In a continuous coating process, continuous flow equipment simultaneously meters both the seed flow and the seed treatment products. A slide gate, cone and orifice, seed wheel, or weight device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed. In a batch coating process, batch treating equipment weighs out a prescribed amount of seed and places the seed into a closed treating chamber or bowl where the corresponding of seed treatment is then applied. The seed and seed treatment are then mixed to achieve a substantially uniform coating on each seed. This batch is then dumped out of the treating chamber in preparation for the treatment of the next batch. With computer control systems, this batch process is automated enabling it to continuously repeat the batch treating process. In either coating process, the seed coating machinery can optionally be operated by a programmable logic controller that allows various equipment to be started and stopped without employee intervention.

In another embodiment, the seed or soil treatment agricultural composition along with one or more optional components are formulated as a soil treatment. The soil treatment may be in addition to, or as a substitute for, the seed treatment. Soil may be treated by application of the desired agricultural composition to the soil by conventional methods such as spraying. Alternatively, the desired composition can be introduced to the soil before germination of the seed or directly to the soil in contact with the roots by utilizing a variety of techniques included, but not limited to, drip irrigation, sprinklers, soil injection or soil drenching. The desired agricultural composition may be applied to the soil before planting, at the time of planting, or after planting.

The present invention is explained in greater detail in the following non-limiting Example.

EXAMPLE

In this example, we disclose the (1) the formulation and characterization of TMGMV loaded with crystal violet (CV) ($_{CV}$TMGMV), (2) the bioavailability and treatment efficacy of $_{CV}$TMGMV in nematodes in liquid culture compared to free CV, and (3) the soil mobility of $_{CV}$TMGMV compared to free CV.

METHODS

CV Loading into TMGMV

TMGMV was obtained from Bioprodex. CV (G2039, Sigma-Aldrich) was loaded into the interior channel of TMGMV through electrostatic interactions between the positively charged drug and the negatively charged Glu and Asp. TMGMV (1 mg·mL$^{-1}$ final concentration, in 10 mM potassium phosphate (KP) buffer, pH 7.8) was incubated with CV using a molar excess of 500:1, 1000:1, 2000:1, 3000:1, 4000:1, 6000:1, 10,000:1, or 20,000:1 CV:TMGMV overnight at room temperature with agitation. The reaction mix was purified over a 40% (w/v) sucrose cushion using an Optima MAX-TL ultracentrifuge (Beckman) and a TL-55 rotor at 50,000 rpm for 1 h to yield pure $_{CV}$TMGMV. Particles were resuspended in 10 mM KP buffer (pH 7.8) overnight at 4° C., and the remaining particle aggregates were removed by centrifugation at 12,000 rpm for 10 min using a table top ultracentrifuge. CVTMGMV nanoparticles were analyzed using a combination of UV-vis spectroscopy, SDS-polyacrylamide gel electrophoresis (SDS-Nu-PAGE), TEM, and SEC; see below. To confirm that CV was indeed interacting with Glu and Asp, chemically modified TMGMV in which the interior Glu/Asp side chains were neutralized was utilized; see below.

Bioconjugation of TMGMV Glutamic/Aspartic Acid Residues

First, alkynes were conjugated to the internal TMGMV carboxylate groups using 25 equiv of propargylamine (P50900; Sigma-Aldrich) per CP and 45 equiv of EDC (with 22.5 equiv added at t=0 and 12 h) in 10 mM HEPES buffer (pH 7.4). The reaction was allowed to proceed for 24 h at room temperature. Second, an alkyne-azide click reaction was performed by adding 2 equiv of sulfocyanine5-azide (B3330; Lumiprobe) or 5 equiv of biotin-azide (875770, Sigma-Aldrich) per CP. Click reactions were conducted on ice for 30 min using 2 mg·mL–1 of TMGMV in 10 mM KP buffer (pH 7.4) in the presence of 1 mM CuSO4 (AC423615000, Fisher), 2 mM AMG (AC36891025, Fisher), and 2 mM Asc (AC352681000, Fisher). $_{Glu/Asp-Cy5}$TMGMV and $_{Glu/Asp/biotin}$TMGMV were purified using by ultracentrifugation at 50,000 rpm for 1 h on a 40% (w/v) sucrose cushion. Particles were resuspended in 10 mM KP buffer (pH 7.4) overnight at 4° C., and the remaining particle aggregates were removed by centrifugation at 12,000 rpm for 10 min using a table top ultracentrifuge. $_{Glu/Asp-Cy5}$TMGMV and $_{Glu/Asp/biotin}$TMGMV nanoparticles were analyzed using a combination of UV-vis spectroscopy, gel electrophoresis, and Western blotting; see below.

Bioconjugation of TMGMV Tyrosine Residues

First, a diazonium salt was formed by reacting 75 μL of 3 M sodium nitrite (237213, Sigma-Aldrich) with 25 μL of 0.68 M 3-ethylaniline (498289, Sigma-Aldrich) in a final volume of 400 μL of 0.3 M p-toluenesulfonic acid monohydrate (AC139025000, Fisher) for 1 h on ice. Fifteen equiv of the in situ formed diazonium salt was added to a 2 mg·mL$^{-1}$ final concentration of TMGMV in 10 mM borate buffer (pH 8.8) for 30 min on ice. Particles were purified using by ultracentrifugation at 50,000 rpm for 1 h on a 40% (w/v) sucrose cushion. Particles were resuspended in 10 mM KP buffer (pH 7.4) overnight at 4° C., and the remaining particle aggregates were removed by centrifugation at 12,000 rpm for 10 min using a table top ultracentrifuge. Second, an alkyne-azide click reaction was performed by adding 2 equiv of sulfocyanine5-azide (B3330; Lumiprobe) per CP. Particles were purified using the previously described method. Tyr-Cy5TMGMV nanoparticles were analyzed using a combination of UV-vis spectroscopy and gel electrophoresis; see below.

UV-Vis Spectroscopy

A NanoDrop spectrophotometer (Thermo Scientific) was used to measure the UV-vis spectra of native and modified TMGMV nanoparticles. The amount of CV or Cy5 fluorophore per TMGMV CP was determined based on the ratio of molecule:TMGMV CP concentration and the use of the Beer-Lambert law. CV-, Cy5-, and TMGMV-specific extinction coefficients are as follows: TMGMV: ε(260 nm)=3 mL·mg$^{-1}$ cm$^{-1}$, molecular weight of TMGMV=39.4×10$^6$ g mol$^{-1}$; Cy5: ε(651 nm)=270,000 M$^{-1}$·cm$^{-1}$, molecular weight of Cy5=747 g·mol$^{-1}$; CV: ε(590 nm)=87,000 M$^{-1}$·cm$^{-1}$, molecular weight of CV=407.98 g·mol$^{-1}$

Denaturing Gel Electrophoresis (SDS-NuPAGE)

Twenty μg of TMGMV control, $_{CV}$TMGMV, $_{Glu/Asp/biotin}$TMGMV+CV, $_{Glu/Asp/Cy5}$TMGMV, and $_{Tyr-Cy5}$TMGMV were denatured at 100° C. for 5 min in 4× LDS loading dye (NP0008, Life Technologies) to obtain a final volume of 12 μL. TMGMV proteins, as well as SeeBlue Plus2 ladder (LC5925, Life Technologies), were separated for 40 min at 200 V and 120 mA using a 4-12% NuPAGE precast gel in 1× MOPS buffer (NP0001-02, Life Technologies). Gels were photographed before and after staining with Coomassie Blue (0.25% w/v) using the AlphaImager (Biosciences) imaging system under white light.

Western Blotting

TMGMV and $_{Glu/Asp/biotin}$TMGMV samples separated by denaturing gel electrophoresis (see above) were transformed from the gel onto a nitro-cellulose membrane under a constant voltage of 30 V for 1 h. The membrane was then incubated in blocking buffer made of 5% (w/v) milk in TBST (150 mM NaCl, 50 mM Tris HCl, 0.2% (v/v) Tween-20, pH 7.5) overnight at 4° C. Then, the membrane was incubated with 1:2000 streptavidin-alkaline phosphatase (S2890, Sigma-Aldrich) in blocking solution for 1 h at room temperature and subsequently washed 3 times in TBST. Antibody binding was visualized using Novex AP Chromogenic Substrate (BCIP/NBT) (WP20001, Invitrogen).

Size Exclusion Chromatography

Samples (200 μL of 1 mg·mL$^{-1}$) were analyzed through a Superose6 column on the AKTA Explorer chromatography system (GE Healthcare) using a flow rate 0.5 mL·min$^{-1}$ in 10 mM KP (pH 7.4). The absorbance at 260 and 280 nm was recorded.

Transmission Electron Microscopy

Drops of TMGMV particles (20 μL, 1 mg·mL$^{-1}$) were added to Formvar carbon film coated copper TEM grids (FCF400-CU, Electron Microscopy Sciences) for 2 min at room temperature. The grids were washed twice with deionized water for 30 s and subsequently stained twice with 2% (w/v) uranyl acetate in deionized water for another 45 s. A Tecnai F30 transmission electron microscope was used to inspect samples at 300 kV.

CV Release Profile from CVTMGMV

The release of CV from TMGMV was evaluated using a dialysis-based assay. One milligram of $_{CV}$TMGMV in 10 mM KP (pH 7.8) was loaded in triplicates in Slide-A-Lyzer MINI dialysis units (69570, Fisher) with a 10,000 MW cutoff membrane. $_{CV}$TMGMV was dialyzed against various buffers at room temperature and at 4° C. for 72 h. At specific time points (t=0, 1, 3, 6, 18, 24, 48, and 72 h), 10 μL was extracted from each dialysis units and analyzed using UV-vis spectroscopy to quantify the release of CV from $_{CV}$TMGMV.

*C. elegans* Nematode Culture

OP50-1 *E. coli* and *C. elegans* strain N2 were provided by the *Caenorhabditis* Genetics Center (CGC) from the University of Minnesota, which is funded by NIH office of Research Infrastructure Programs P40 OD010440. Nematodes were cultured using 100 mm×15 mm sterile polystyrene Petri dishes (FB0875712, Fisher). Plates were seeded with agar (3 g of NaCl, 17 g of agar (BP1425, Fisher), 2.5 g of peptone (BP1420-2, Fischer) in 1 L of $H_2O$) supplemented with 1 mL of 1 M $MgSO_4$ (M65-500, Fisher), 1 mL of 1 M $CaCl_2$ (BP510, Fisher), 1 mL of 5 mg·mL−1 cholesterol (C3045, Sigma-Aldrich), 25 mL of 1 M KPO4, 50 mg·mL$^{-1}$ streptomycin (11860-038, Fisher), and subsequently cultured with OP50-1 *E. coli* at 37° C. for 8 h. Nematodes were then cultured on the OP50-1 *E. coli* plates at 22° C. Alternatively, nematodes were maintained in a liquid culture of S Basal (5.85 g of NaCl, 1 g of $K_2HPO_4$, 6 g of $KH_2PO_4$, and 1 mL of 5 mg·mL$^{-1}$ cholesterol in 1 L of $H_2O$) supplemented with 10 mL of 1 M potassium citrate (7788-99-0, Fisher) pH 6, 10 mL of trace metals solution (N1010, US Biological), 3 mL of 1 M $MgSO_4$, 3 mL of 1 M $CaCl_2$, and 50 mg·mL$^{-1}$ of streptomycin. OP50-1 *E. coli* pellet stocks were resuspended in S basal and added to the liquid culture to provide a food source to the nematodes.

Bioavailability of $_{CV}$TMGMV and Free CV to *C. elegans*

Bioavailability of $_{CV}$TMGMV and free CV to *C. elegans* was investigated in liquid culture (see above). 50 Nematodes were added to each well of a 24-well culture plate to a final volume of 1 mL. Nematodes were treated in triplicates with 0, 0.01, 0.1, 1, 10, and 100 μM of CV for a period of 24 h at 22° C. At specific time points (t=0, 1, 3, 6, 18, and 24 h), nematodes were observed under a white light microscope (magnification=5×), and their motility was classified between (1) totally immobilized nematodes, (2) nematodes with impaired mobility, and (3) completely mobilized nematodes. The percent of affected nematodes (sum of the nematodes on scale (2) and (3)) as a function of time and the effective concentration (EC50) were determined comparing free CV, TMGMV, and $_{CV}$TMGMV.

Soil Mobility of $_{CV}$TMGMV and Free CV

The following soil mobility test was designed to establish the leaching of $_{CV}$TMGMV and free CV in a soil column. Top Soil (5540, Garden Magic) was packed in a plastic column up to a height of 4 cm and saturated with DI water. One mL aliquots of $_{CV}$TMGMV or free CV (the concentration was 100 mM normalized to the drug concentration) were applied atop of the soil columns, followed by 50 elution fractions of 300 μL DI water. Each collected elution fraction was centrifuged for 10 min at 12,000 rpm to precipitate remaining soil particles. The supernatant was subsequently analyzed by UV-vis spectroscopy (see above).

Results

Synthesis and Charcterization of TMGMV-Encapsulated CV

TMGMV is the U2 strain of TMV; the latter has been extensively studied in plant pathology and structural biology since the 1900s and more recently in nanomedicine, biotechnology, and energy research. Therefore, the surface chemistry of TMV is well understood. Here we set out to establish the chemistry of TMGMV. The amino acid sequences of the coat proteins (CPs) of TMV and TMGMV present 72% homology; also the structural overlay of a single CP of TMV and TMGMV reveals a high degree of structural similarity; only 14% of the amino acids do not overlap in the crystal structures (PDB: 2TMV for TMV; 1VTM for TMGMV). This is also reflected when comparing the assembled nucleoprotein complexes of TMV and TMGMV (FIG. 1). Just like TMV, TMGMV forms a cylindrical structure measuring 300×18 nm with a 4 nm-wide hollow interior channel. The TMGMV particles consist of 2130 identical copies of CP units arranged helically around a single-stranded RNA genome (FIGS. 1A, B). Analysis of the structure reveals the amino acid profile on the exterior and interior surface: because Lys, Cys, Tyr, Asp, and Glu are often targeted for bioconjugation or electrostatic drug loading, we analyzed the TMGMV structure for presence of these residues. While solvent-exposed Lys and Cys side chains were not identified in TMGMV, several Tyr, Asp, and Glu residues were found to be solvent exposed on the exterior/interior TMGMV surfaces. Structural data indicate Tyr2 to be exposed on the exterior surface; this is different from the structure of TMV, for which both Tyr2 and to a greater extent Tyr139 are solvent exposed on the exterior surface. The Tyr2 side chain of TMGMV could provide a potential target for bioconjugation, e.g., the introduction of a fluorescent label for imaging and tracking studies as described below. Further, we identified Asp66 and Glu95, 106, and 145 to be solvent exposed, with Glu145 and Asp66 located on the exterior surface and Glu95 and Glu106 on the interior surface (FIGS. 1C, D). This is similar to the structure of TMV, for which Glu145, Asp64, and Asp66 are solvent exposed on the exterior surface, while Glu97 and Glu106 are solvent exposed on the interior surface. However, it should be noted that previous research identified Glu97 and Glu106 to be the only carboxylates in TMV that are reactive toward carboxylate-specific chemistries; Glu145 and Asp64 and 66 were not found to be reactive. The presence of Glu/Asp residues in TMGMV would allow for functionalization through bioconjugate chemistry or electrostatic loading of positively charged guest molecules, as we previously described in the case of TMV. Lastly, we analyzed the surface charge of TMGMV and determined that the inner and outer surfaces carry a net negative Coulombic charge with the interior being more electronegative than the exterior (FIGS. 1E,F). Together these data indicate solvent-exposed Tyr side chains on the exterior surface of TMGMV and addressable carboxylates, possibly on the exterior and interior surfaces.

With the structural information in hand, we set out to develop TMGMV as a carrier for nematicide delivery. Specifically, we chose to work with CV as a proof-of-concept, because this therapeutic compound is fluorescent and thus streamlines the analysis. The positively charged CV was loaded into TMGMV making use of electrostatic interactions and concepts that were previously developed to load positively charged platinum drug candidates and porphyrin derivatives into TMV.

To load CV into TMGMV, the following protocol was established: TMGMV was incubated with CV using a molar excess of 500:1, 1000:1, 2000:1, 3000:1, 4000:1, 6000:1, 10,000:1, 20,000:1 CV:TMGMV in 10 mM potassium phosphate (KP) buffer (pH 7.8) overnight at room temperature with agitation (at pH 7.8, the majority of the carboxylate groups is deprotonated and thus carries a net negative charge allowing interaction with the positively charged CV guest molecule). The reaction mix was purified by ultracentrifugation over a sucrose cushion to yield pure $_{CV}$TMGMV, and the degree of labeling with CV was subsequently quantified by UV-vis spectroscopy based on the Beer-Lambert law and CV-, TMGMV-specific extinction coefficients (FIGS. 3A,B). CV loading efficiency in TMGMV increased with the excess of CV to TMGMV used; a plateau was not reached. Nonetheless, we observed substantial aggregate formation of free CV/$_{CV}$TMGMV when an excess of 10,000:1 or 20,000:1

CV:TMGMV mixtures were purified, therefore these samples were not considered for further evaluation. The reaction mix of 6000:1 CV:TMGMV resulted in the highest loading efficiency while still yielding dispersed TMGMV particles: 68% of the CPs were modified with a CV molecule. Assuming a full length TMGMV particle (300×18 nm), each TMGMV would carry about 1500 drug molecules. This formulation was subsequently used for all following studies.

When compared with TMV-drug formulations, the TMGMV formulation yielded comparable results: we previously reported the loading of 2000 phenanthriplatin per TMV and 900 copies of a porphyrin derivative ZnPr per TMV. In those cases, the loading procedure was similar, in which a positively charged guest molecule was loaded via electrostatic interaction with TMV's interior carboxylates. As in the case of TMV, the interior channel of TMGMV is lined with a dense layer of carboxylates; this, in combination with the more electronegative interior surface, may suggest that drug loading occurs on the inside channel. However, further studies would be needed to rule out drug association with the exterior surface in both the cases of TMV and TMGMV. To compare the drug loading efficiency of the rod-shaped TMGMV system to the icosahedral (sphere-like) RCNMV-based nematicide carrier, the number of drug molecules was normalized to the molecular weight of the nanocarrier yielding about $3.6×10^{-5}$ CV per dalton of TMGMV protein, while only about $1.8×10^{-5}$ abamectin molecules were loaded per dalton of RCNMV protein. In other words, when normalized per molecular weight, twice as much drug molecule can be loaded per TMGMV than compared to RCNMV.

The structural integrity of nonmodified TMGMV and $_{CV}$TMGMV was assessed by size exclusion chromatography (SEC) and transmission electron microscopy (TEM). SEC measurements revealed no significant difference comparing native TMGMV and $_{CV}$TMGMV; both particles showed the same elution profile (elution at 8 mL volume) (FIGS. 3E,F). Further, TEM imaging of TMGMV and $_{CV}$TMGMV revealed rod-shaped samples with no apparent differences when comparing TMGMV and $_{CV}$TMGMV (FIGS. 3G,H); TEM imaging indicates that the average length of TMGMV and $_{CV}$TMGMV is comparable, measuring 146±97 nm and 136±76 nm, respectively. It should be noted that short, broken particles were observed both pre- and postdrug loading. It is possible that this is an artifact from the TEM grid preparation, i.e., the particles may break during the drying process. However, it is important to note that there are no apparent differences comparing the TMGMV and $_{CV}$TMGMV, indicating that the nucleoprotein complex withstands the loading and purification process.

To gain insights into whether CV-loading into TMGMV is indeed via electrostatic interactions with Glu and/or Asp residues, chemically modified TMGMV in which the carboxylates were neutralized was prepared. To do so, EDC coupling was used to introduce alkyne ligands at the carboxylates, for subsequent addition of biotin labels using Cu(I)-catalyzed alkyne-azide cycloaddition (click chemistry) (FIGS. 2C,D). The protocols are detailed in the methods and were adapted from previous methods established for bioconjugation to TMV. Biotinylation was confirmed by Western blot (FIG. 3D), yet quantitative data could not be obtained. To quantify the degree of labeling, the fluorescent Cy5 dye was conjugated to $_{Glu/Asp}$TMGMV, yielding about 275 dyes per full length TMGMV, or about 13% of CPs were modified with Cy5. Biotinylated and alkyne-labeled TMGMV were then used in CV-loading experiments, and we observed a 40% decrease in CV loading when using alkynelabeled TMGMV compared to unmodified $_{Glu/Asp}$TMGMV (FIG. 3C). Severe aggregation was observed when biotinylated TMGMV was used in CV loading experiments (FIG. 3D). This phenomenon may be explained as follows: if the chemistry of TMGMV and TMV is matched, then biotins will be displayed along the interior channel, preventing the positively charged guest molecules to be loaded and protected inside the TMGMV channel; instead CV may cross-link the particles through interactions with the less negative, also negatively charged exterior surface. Because the data indicate that CV-loading is mediated through the solvent-exposed Glu/Asp acids, and in light of the TMGMV structure (FIG. 1) and its similarities to the known biochemistry to TMV, we therefore expect that interior loading of CV is achieved by this method.

Next, we evaluated the release profile of CV from the TMGMV nanocarrier. The release rate of CV from $_{CV}$TMGMV is expected to be proportional to the pH of the bathing conditions as well as temperature. Based on thermodynamics, the rate of diffusion should increase with temperature. Furthermore, as pH decreases, a larger number of carboxylate groups become protonated and carry a net neutral charge that can no longer interact with the positively charge CV and consequently, free CV should diffuse away from TMGMV. Therefore, the release rate of CV should be higher at lower pH and higher temperatures. To test this experimentally, 1 mg of a 1 mg·mL$^{-1}$ solution of CVTMGMV was prepared as described above and dialyzed against various buffers for 72 h (FIG. 4A). We tested the release profile at room temperature and 4° C. to evaluate two extreme upper soil thermal conditions. Sodium acetate (pH 5.2) and PBS (pH 7.4) buffer solutions were chosen to mimic the acidic and neutral soil environments, respectively. Diffusion of CV from CVTMGMV was also evaluated in KP (pH 7.8) buffer, which was used during loading and storing conditions of the sample. Free CV, in a concentration matched to the concentration and number loaded into TMGMV, was also dialyzed in KP buffer (pH 7.8) at 4° C. as a positive control.

As expected, increased release rates of CV from $_{CV}$TMGMV were observed at low pH and high temperature (FIG. 4). Approximately half of the free CV (brown) was dialyzed within 1.6 h, and complete release was observed in <18 h, while delayed release profiles were observed for the CVTMGMV nanoparticle formulations. For CVTMGMV, 50% of CV was released only after 5 h in acidic conditions (10 mM acetate buffer, pH 5.2) at room temperature (black), with complete release achieved after about 24 h. These conditions most realistically mimic the soil environment. In stark contrast, release in storing conditions (10 mM KP, pH 7.8, 4° C.) was significantly slower, with 50% of CV released within 13 h, and complete release was not observed within 72 h. This is promising for application of these nanoparticles, however it would be advised to prepare fresh formulations before application in the field.

We have previously reported similar results with the release of the cancer drug phenanthriplatin from TMV; half of the encapsulated chemotherapeutic was released after 1 h at pH 5 and 24 h at pH 7.4. On the other hand, encapsulated porphyrin derivatives loaded in TMV were found to be stably encapsulated for at least one month when stored at 4° C. and pH 7. We hypothesize that the increase in stability of the porphyrin drug was due to its higher electropositivity: the compound used carries 3 positive charges. In contrast, phenanthriplatin and CV carry 2 and 1 positive charges, respectively. Compared to the previously reported RCNMV carrier, the release rate of CV from TMGMV is slightly faster than that of abamectin from RCNMV in acidic soil conditions. 50% of abamectin was released within 8 and 7 h at pH 5.2 and 7.4, respectively (vs 50% of CV released after 5 and 7 h under the same conditions).

$_{CV}$TMGMV Toxicity and Interactions with *Caenorhabditis elegans* Nematodes

Bioavailability of $_{CV}$TMGMV and free CV in *Caenorhabditis elegans* (*C. elegans*) was investigated in liquid culture. *C. elegans* nematode motility was classified as either (1) totally immobilized, (2) impaired motility, or (3) completely mobilized nematodes. To illustrate the data that were collected, a series of snap shots of *C. elegans* incubated with no treatment, 10 μM of CV, and 10 μM of $_{CV}$TMGMV were taken every second for 60 s. FIGS. 5A-C illustrate the nematodes observed after 3 h of incubation. Five nematodes were selected in each treatment regime and pseudocolored to illustrate their motility. Untreated *C. elegans* showed no impaired motility (FIG. 5A). For example, the nematode colored in pink moves across the frame within the 40 s interval, while other nematodes disappear from or appear in the frame during that time interval. Although the motility of these nematodes is evident, most nematodes do not travel far but rather move within a restricted area, such as the nematode colored in yellow. *C. elegans* treated with 10 μM of CV or 10 μM of CVTMGMV behaved differently and showed severe motility impairment (FIGS. 5B, C). All pseudocolored nematodes in FIGS. 5B,C were paralyzed or dead and did not move. However, this is not true for all nematodes, as a population of nematodes showed little to no motility impairment when treated with CV or $_{CV}$TMGMV. From the imaging data, there were no apparent differences between the two treatment groups, free drug vs $_{CV}$TMGMV (FIGS. 5B, C).

To quantitatively analyze the motility effects of CV on *C. elegans*, nematodes were treated with various concentrations (0, 0.01, 0.1, 1, 10, and 100 μM) of free CV, $_{CV}$TMGMV, or TMGMV for 24 h at 22° C. At specific time points, nematodes were observed under a white light microscope, and the percent of affected nematodes (sum of the nematodes on scale (2) and (3)) was quantified as a function of time. The effective concentration (EC50), defined as the concentration of CV at which half of the maximum immobilization of *C. elegans* was reached, was determined for free CV and CVTMGMV (FIGS. 5D-G). Sixty % of nematodes treated with 100 μM of CV were paralyzed/dead within 1 h, and no further improvements were observed within 24 h (FIG. 5D). When treated with 10 μM or 1 μM of CV, only about 30% or about 15% of nematodes were paralyzed/dead within the first hour, respectively. In those cases, maximum efficacy was observed after 6 h of incubation, when about 50% (10 μM of CV) and about 25% (1 μM of CV) of nematodes were affected. In both treatment regimes, a decrease in efficacy was observed after 6 h of incubation; this phenomenon may be explained because the remaining unaffected population of nematodes continued to progress through their life cycle; consequently eggs were laid and nematodes hatched, which led to an overall increase in population and a decrease in percent of nematodes affected by the treatment. Furthermore, it is possible that at low doses of CV, nematodes are able to recover and slowly become mobile again. At doses of CV lower than 1 μM, there was no significant effect on nematode motility compared to the untreated population. The EC50 was quantified at various time points and was determined to be 3.7 μM. CVTMGMV showed a similar trend to free CV (FIGS. 5F, G), and, as expected, TMGMV alone did not show any nematicide properties. When treated with 100 μM of $_{CV}$TMGMV, about 40% of nematodes were paralyzed/dead within the first hour, and maximum efficacy (about 60%) was reached in the first 3 h. Therefore, the efficacy of 100 μM of CV and $_{CV}$TMGMV is identical after 3 h of incubation. However, when the concentration of $_{CV}$TMGMV was dropped to 10 μM, the maximum efficacy was about 30% and was reached after about 8 h of incubation. Interestingly, CV release from $_{CV}$TMGMV in nematode media conditions revealed a half-life of 8 h (FIG. 4), thus supporting the idea that CV was released from TMGMV and made available to treat the nematode infestation. All studied concentrations of $_{CV}$TMGMV lower than 10 μM led to no significant treatment of the nematode infestation compared to the untreated population. The calculated EC50 of $_{CV}$TMGMV is 13.8 μM, which is approximately 4 times greater than the EC50 of free CV. While reduced efficacy was observed in the Petri dish experiments, we envision that $_{CV}$TMGMV will outperform free CV in the field based on the enhanced drug delivery aspect.

Next, we set out to understand the biodistribution of CV in the nematodes. We prepared fluorescently labeled TMGMV and analyzed whether TMGMV would interact with or be ingested by *C. elegans*. Briefly, diazonium coupling and click chemistry was used to conjugate a Cy5 dye to Tyr side chains on TMGMV, as structural studies indicated that Tyr2 is solvent exposed (FIGS. 1 and 6A). We conjugated ~160 dyes per full length TMGMV, or about 7.5% of CPs were modified with Cy5. We have previously demonstrated that a minimum conjugation of Cy5 to about 8% of TMV CPs is sufficient to yield maximum fluorescence intensity, thus the prepared samples were thought to be sufficient for imaging experiments. Fluorescent $_{Tyr-Cy5}$TMGMV was incubated with *C. elegans* nematodes for 3 h at 22° C. and subsequently analyzed by fluorescent microscopy (FIG. 6B,C). Results indicate that nematodes ingest the proteinaceous TMGMV carrier and that while TMGMV distributes throughout the entire nematode body, the majority of TMGMV accumulates in the gastrointestinal (GI) tract.

Soil Mobility of $_{CV}$TMGMV and Free CV

A soil mobility test was designed to establish the leaching of $_{CV}$TMGMV and free CV in soil. Briefly, top soil was packed in a plastic column up to a height of 4 cm and saturated with deionized (DI) water. $_{CV}$TMGMV or free CV was applied atop the soil columns, followed by DI water. Fractions were collected from the soil column, purified, and analyzed by UV-vis spectroscopy for the presence of TMGMV and CV. The λ260 (RNA) and λ280 (CP) wavelengths were monitored to quantify the amount of TMGMV that leached through the soil. A background 260/280 absorbance was observed in a CV soil leaching column, which most likely corresponds to the absorbance of organic matter present in top soil (FIG. 7A). $_{CV}$TMGMV showed enhanced mobility over free CV in the soil column, eluting from the column at high concentrations in the fifth to 15th elution fractions (FIGS. 7B,C). In stark contrast, the efflux of CV from the soil column was delayed until the 25th to 50th elution fractions at a concentration 3.6 times lower than CVTMGMV (FIG. 7D). CV is hydrophobic and has a strong binding affinity to soil particles (Koc=6.1×10⁵, ref: PubChem CID 11057), rendering the drug mostly immobile in soil, which explains the delayed efflux and lower concentrations eluted. Taken together, the data show TMGMV can be used as a drug carrier to enable penetration of CV or other nematicides through soil to reach nematodes feeding on the roots of plants.

In this study, we have demonstrated the potential of tobacco mild green mosaic virus (TMGMV) as a carrier for anthelmintic drugs, such as crystal violet (CV), to treat plants infected with parasitic nematodes. After careful analysis of the TMGMV structure, we identified solvent-exposed Tyr2 on the exterior surface enabling chemical modification. We also identified solvent-exposed carboxylates, Glu145 and Asp66 on the exterior surface and Glu95 and Glu106 on the interior surface, and established the chemical addressability of these residues. We also showed the potential for electrostatic encapsulation of positively charged guest molecules in TMGMV. Further studies are needed to identify which of the identified Glu and Asp residues are chemically reactive. Electrostatic drug loading using CV was achieved, yielding TMGMV carriers loaded with about 1500 CV per CVTMGMV nanocarrier. Treatment efficacy, while lower compared to free drug, was demonstrated using liquid *C. elegans* nematode cultures (EC50=13.8 μM of CVTMGMV vs EC50=3.7 μM for free CV). Diffusion experiments revealed significantly increased soil mobility of CVTMGMV vs free CV; the latter was unable to sufficiently diffuse and disperse through soil. Overall, CVTMGMV demonstrates efficacy and superior soil motility and, as such, makes a promising platform technology as a drug carrier targeting agricultural application.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating a plant, comprising applying an agricultural composition to the plant in a treatment effective amount to combat nematode parasitism on the plant, the agricultural composition including a plurality of tobacco mild green mosaic virus (TMGMV) and/or VLPs thereof, each TMGMV and/or VLP having an interior surface that extends from a first end to a second end of the TMGMV and/or VLP, the interior surface defining a channel that extends through TMGMV and/or VLPs thereof from the first end to the second end; and crystal violet (hexamethyl parparosaniline chloride) non-covalently loaded onto negatively charged interior surface of the TMGMV and/or VLPs by electrostatic interactions, wherein the negatively charged interior surface of the TMGMV and/or VLPs thereof includes a solvent exposed glutamic acid 95 (Glu95) amino acid residue on the interior surface of the TMGMV and/or VLPs thereof.

2. The method of claim 1, wherein the plant is a monocot or dicot.

3. The method of claim 1, wherein the plant is selected from the group consisting of wheat, corn (maize), soybean, cotton, cassava, potato, sweet potato, bananas, citrus, strawberries, tomato, coffee, carrots, peppers, turf grass, and greenhouse ornamentals.

4. The method of claim 1, wherein the plant is a plant part selected from the group consisting of leaves, flowers, stems, roots, tubers, fruits, and seeds.

5. The method of claim 1, wherein the plant is a seed.

6. The method of claim 1, wherein the nematode is selected from the group consisting of *Meloidogyne* root knot nematodes, *Globodera* and *Heterodera* cyst nematodes; *Pratylenchus* lesion nematodies, *Dietylenchus* stem and bulb nematodes, *Tylenchulus* citrus nematodes, *Xiphinema* dagger nematodes, *Radopholus* burrowing nematodes, *Rotylenchulus* reniform nematodes, *Helicotylenchus* spiral nematodes, and *Belonolaimus* sting nematodes.

7. The method of claim 1, wherein the composition is a sprayable composition.

8. The method of claim 1, further comprising a water carrier.

9. The method of claim 1, wherein the composition is applied as a seed coating.

* * * * *